United States Patent
Radley et al.

(10) Patent No.: US 7,209,545 B2
(45) Date of Patent: Apr. 24, 2007

(54) X-RAY SOURCE ASSEMBLY HAVING ENHANCED OUTPUT STABILITY, AND FLUID STREAM ANALYSIS APPLICATIONS THEREOF

(75) Inventors: Ian Radley, Glenmont, NY (US); Thomas J. Bievenue, Delmar, NY (US); John H. Burdett, Jr., Charlton, NY (US); Brian W. Gallagher, Guilderland, NY (US); Stuart M. Shakshober, Hudson, NY (US); Zewu Chen, Schenectady, NY (US); Michael D. Moore, Alplaus, NY (US)

(73) Assignee: X-Ray Optical Systems, Inc., East Greenbush, NY (US)

( * ) Notice: Subject to any disclaimer, the term of this patent is extended or adjusted under 35 U.S.C. 154(b) by 0 days.

(21) Appl. No.: 10/859,901

(22) Filed: Jun. 3, 2004

(65) Prior Publication Data
US 2005/0053197 A1 Mar. 10, 2005

Related U.S. Application Data

(63) Continuation of application No. PCT/US02/38493, filed on Dec. 4, 2002, and a continuation of application No. 10/206,531, filed on Jul. 26, 2002, now Pat. No. 6,781,060.

(60) Provisional application No. 60/398,966, filed on Jul. 26, 2002, provisional application No. 60/398,968, filed on Jul. 26, 2002, provisional application No. 60/398,965, filed on Jul. 26, 2002, provisional application No. 60/383,990, filed on May 29, 2002, provisional application No. 60/336,584, filed on Dec. 4, 2001.

(51) Int. Cl.
 *H01J 35/30* (2006.01)

(52) U.S. Cl. .................................. 378/137; 378/193
(58) Field of Classification Search ........ 378/193–202, 378/137, 125, 127, 129, 205, 4
See application file for complete search history.

(56) References Cited

U.S. PATENT DOCUMENTS

| 2,121,630 A | 6/1938 | Gross et al. .................. 250/34 |
| 2,825,816 A | 3/1958 | Rogers ........................ 250/95 |

(Continued)

FOREIGN PATENT DOCUMENTS

DE 195 40 195 A1 5/1997

(Continued)

*Primary Examiner*—Edward J. Glick
*Assistant Examiner*—Hoon Song
(74) *Attorney, Agent, or Firm*—Jeffrey R. Klembczyk, Esq; Kevin P. Radigan, Esq.; Heslin Rothenberg Farley & Mesiti, P.C.

(57) ABSTRACT

An x-ray source assembly (2700) and method of operation are provided having enhanced output stability. The assembly includes an anode (2125) having a source spot upon which electrons (2120) impinge and a control system (2715/2720) for controlling position of the anode source spot relative to an output structure. The control system can maintain the anode source spot location relative to the output structure (2710) notwithstanding a change in one or more operating conditions of the x-ray source assembly. One aspect of the disclosed invention is most amenable to the analysis of sulfur in petroleum-based fuels.

59 Claims, 22 Drawing Sheets

U.S. PATENT DOCUMENTS

| | | | |
|---|---|---|---|
| 2,831,977 A | 4/1958 | Henke .......................... 250/53 |
| 4,039,811 A | 8/1977 | Ennslin et al. ............... 250/409 |
| 4,172,223 A | 10/1979 | Ishijima et al. ............. 250/272 |
| 4,674,109 A | 6/1987 | Ono ........................... 378/130 |
| 4,837,792 A | 6/1989 | Goethert ........................ 378/4 |
| 4,891,829 A * | 1/1990 | Deckman et al. ............... 378/4 |
| 4,930,145 A | 5/1990 | Sherwin et al. ............. 378/109 |
| 4,979,199 A | 12/1990 | Cueman et al. ............. 378/121 |
| 5,016,267 A | 5/1991 | Wilkins ....................... 378/84 |
| 5,067,146 A * | 11/1991 | Meinel et al. ............... 378/199 |
| 5,177,774 A | 1/1993 | Suckewer et al. ............. 378/43 |
| 5,272,618 A | 12/1993 | Blake .......................... 363/79 |
| 5,550,889 A * | 8/1996 | Gard et al. .................. 378/113 |
| 5,581,591 A * | 12/1996 | Burke et al. ................. 378/135 |
| 5,778,039 A | 7/1998 | Hossain et al. ................ 378/45 |
| 6,185,276 B1 | 2/2001 | Eastman ...................... 378/143 |
| 6,339,635 B1 | 1/2002 | Schardt et al. .............. 378/137 |
| 6,345,086 B1 * | 2/2002 | Ferrandino et al. ........... 378/44 |
| 6,351,520 B1 | 2/2002 | Inazaru ....................... 378/138 |
| 6,577,704 B1 | 6/2003 | Holz ........................... 378/44 |

FOREIGN PATENT DOCUMENTS

| | | |
|---|---|---|
| JP | 05-329143 | 12/1993 |
| WO | WO2001/02842 A2 | 1/2001 |

* cited by examiner

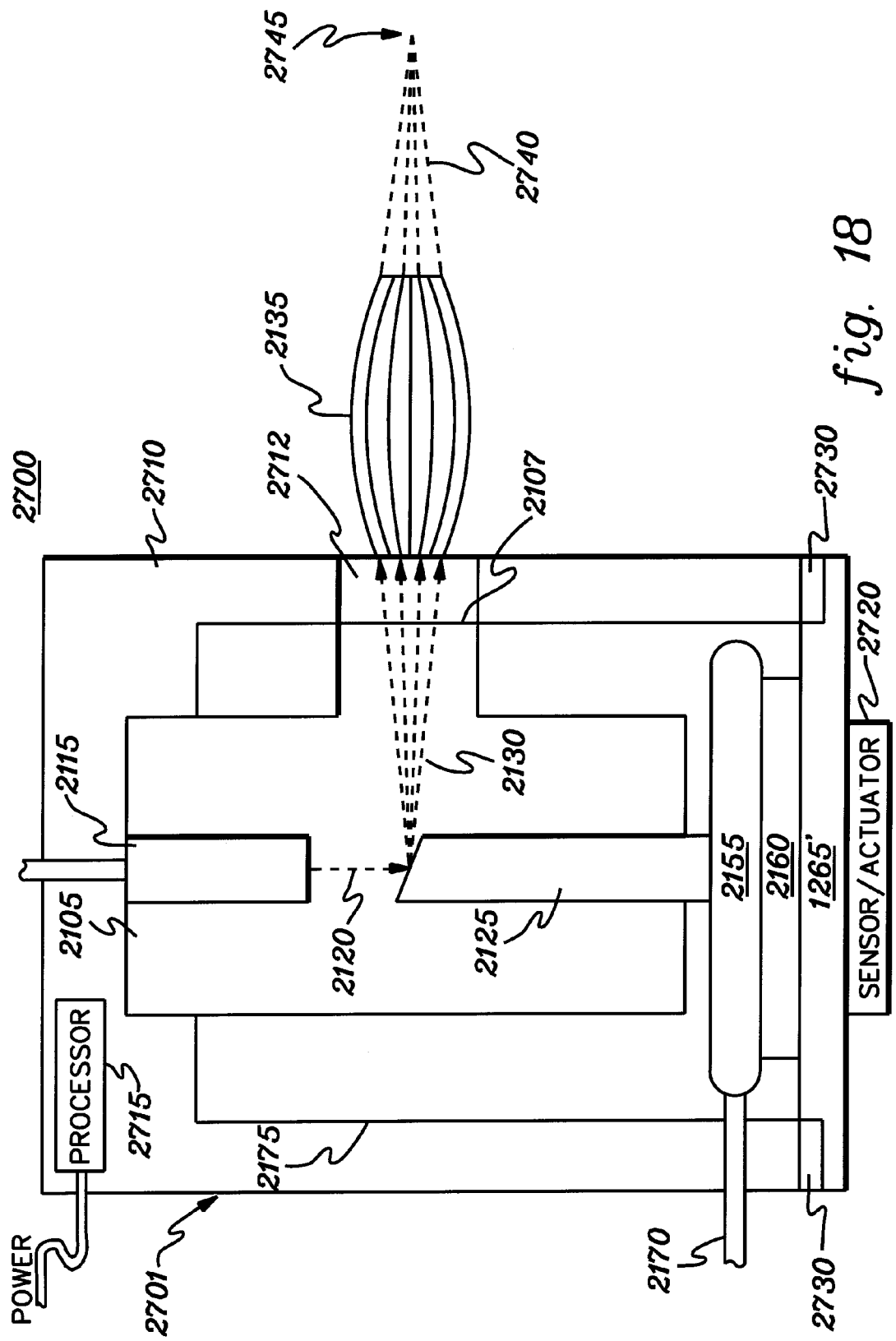

| ANODE POWER LEVEL | HOUSING TEMPERATURE | | | | | | | | | | |
|---|---|---|---|---|---|---|---|---|---|---|---|
| | 20° | 21° | 22° | 23° | 24° | 25° | 26° | 27° | 28° | 29° | 30° |
| 0W | | | | | | | | | | | |
| 10W | | | | | | | | | | | |
| 20W | | | | | | | | | | | |
| ⋮ | ⋮ | ⋮ | ⋮ | ⋮ | ⋮ | ⋮ | ⋮ | ⋮ | ⋮ | ⋮ | ⋮ |
| 100W | | | | | | | | | | | |

X-RAY SOURCE ASSEMBLY HAVING ENHANCED OUTPUT STABILITY, AND FLUID STREAM ANALYSIS APPLICATIONS THEREOF

CROSS-REFERENCE TO RELATED APPLICATIONS

This application is a continuation of PCT Application PCT/US2002/038493, filed Dec. 4, 2002, and published under PCT Article 21(2) in English as WO 2003/049510 A3 on Jun. 12, 2003. PCT/US2002/038493 claimed the priority of the United States applications identified below, which are assigned to the same assignee as this application. The entire disclosures of PCT/US2002/038493 and the below-listed applications are hereby incorporated herein by reference in their entirety:

"X-RAY TUBE AND METHOD AND APPARATUS FOR ANALYZING FLUID STREAMS USING X-RAYS" by Radley, et al. U.S. Ser. No. 60/336,584 filed Dec. 4, 2001;

"A METHOD AND APPARATUS FOR DIRECTING X-RAYS" by Radley, U.S. Ser. No. 60/383,990 filed May 29, 2002;

"X-RAY SOURCE ASSEMBLY HAVING ENHANCED OUTPUT STABILITY" by Radley, et al., U.S. Ser. No. 60/398,965 filed Jul. 26, 2002;

"METHOD AND DEVICE FOR COOLING AND ELECTRICALLY INSULATING A HIGH-VOLTAGE, HEAT-GENERATING COMPONENT" by Radley, U.S. Ser. No. 60/398,968 filed Jul. 26, 2002;

"AN ELECTRICAL CONNECTOR, A CABLE SLEEVE, AND A METHOD FOR FABRICATING AN ELECTRICAL CONNECTION" by Radley, U.S. Ser. No. 10/206,531 filed Jul. 26, 2002 now U.S. Pat. No. 6,781,060; and "DIAGNOSING SYSTEM FOR AN X-RAY SOURCE ASSEMBLY" by Radley, et al., U.S. Ser. No. 60/398,966 filed Jul. 26, 2002.

STATEMENT AS TO RIGHTS UNDER FEDERALLY SPONSORED RESEARCH

This invention was made with Government support under Prime Contract DE-FG02-96ER82918 awarded by the Department of Energy. The United States Government has certain rights to this invention.

TECHNICAL FIELD

The present invention relates generally to x-ray sources, and more particularly, to x-ray source assemblies having a focused or collimated x-ray beam output with enhanced stability over a range of operating conditions; with special application in fluid stream analysis.

BACKGROUND OF THE INVENTION

The implementation of x-ray analysis methods has been one of the most significant developments in twentieth-century science and technology. The use of x-ray diffraction, x-ray spectroscopy, x-ray imaging, and other x-ray analysis techniques has led to a profound increase in knowledge in virtually all scientific fields.

X-ray fluorescence (XRF) is an analytical technique by which a substance is exposed to a beam of x-rays to determine, for example, the presence of certain chemicals. In the XRF technique, at least some of the chemical constituents of the substance exposed to x-rays can absorb x-ray photons and produce characteristic secondary fluorescence x-rays. These secondary x-rays are characteristic of the chemical constituents in the substance. Upon appropriate detection and analysis these secondary x-rays can be used to characterize one or more of the chemical constituents of the substance. The XRF technique has broad applications in many chemical and material science fields, including medical analysis, semiconductor chip evaluation, and forensics, among others.

XRF methods have often been used for measuring the sulfur content of fuels, for example, petroleum-based fuels, such as gasoline and diesel fuels. Existing XRF systems have been known to detect sulfur in fuels down to as low as 5 parts per million (ppm) by weight; however, this detectability has required stringent control conditions, for example, this detectability is typically achievable only in the laboratory. Under less rigorous conditions, for example, in the field, existing XRF methods, such as ASTM standard method D2622, are limited to detecting sulfur concentrations in fuels only down to about 30 ppm. Among other things, the present invention provides improvements in repeatability and detectability of XRF detection of sulfur in fuels.

In these and many other industries, for example, the analytical industry, x-ray beam generating devices are commonly used. X-ray beam generating devices may typically include x-ray tubes which generate x-rays by impinging electron beams onto metal surfaces. X-ray tubes typically include an electron gun which generates an electron beam and an anode which provides the metal surface upon which the electron beam is directed. Typically, the electron gun and anode are operated in three different modes: 1) with a grounded anode and the electron gun operated at high positive voltage; 2) with a grounded electron gun (that is, a grounded cathode) and the anode operated at high negative voltage; or 3) in a "bi-polar" mode with cathode and anode operated at different voltages. For low power applications, the x-ray tube is typically operated with a "grounded cathode" wherein the electron gun and its adjacent components are operated at essentially ground potential and the anode and its adjacent components, if any, at high electric potential, for example, at 50 kilovolts (kv) or higher.

The impingement of the electron beam on the anode and the operation of the anode at such high voltages generates heat, typically a lot of heat, for example, at least about 50 Watts. In order to dissipate this heat, an x-ray tube is typically immersed in a cooling fluid, that is, a thermally-conductive cooling fluid, such as a cooling oil having a high enough dielectric strength to prevent the cooling oil from breaking down and permitting arcing at high potential. A typical high-dielectric cooling fluid is Diala Ax oil provided by Shell Oil Company.

In the conventional art, the x-ray tube and the cooling oil are typically held inside a sealed container, for example, a cylindrical metal container, wherein the x-ray tube is immersed in oil and electrically isolated from the container. The resulting structure includes an x-ray tube having a high-temperature anode at high potential surrounded by a high dielectric strength oil, all encased inside a sealed metal container. As a result, the oil typically convects inside the container as it is heated by the anode. This heating of the oil through convection also heats the walls of the container and the x-ray tube itself via convection. Conventionally, the outside walls of the sealed container may be cooled directly by, for example, natural convection, forced air convection, or flowing a cooling fluid over the outside of the container. This chain of convective and conductive heat transfer is an inefficient cooling process. Even for a conventional x-ray tube requiring modest power dissipation, the x-ray beam device and its components typically reach high temperatures, for example, as much as 120 degrees C. Such high temperatures are undesirable and can be detrimental to the operation of the x-ray tube.

Thus, there is a need in the art to provide simplified methods for cooling an x-ray beam device, or any other high-temperature, high voltage devices.

Moreover, the ability to focus x-ray radiation, until recently unachievable, has enabled reductions in the size and cost of x-ray sources, and hence x-ray systems, that find use in a variety of applications. U.S. Pat. No. 6,351,520 describes one example of an x-ray source which includes a focusing element that enables the production of a high intensity, small diameter x-ray spot size while incorporating a low-power, reduced-cost x-ray source.

While progress in the ability to focus x-ray radiation has recently been achieved, there remains a need for further enhancements to x-ray source assemblies, for example, to improve output stability of an x-ray beam under a variety of operating conditions. The present invention is directed to meeting this need.

SUMMARY OF THE INVENTION

The present invention provides methods and apparatus which address many of the limitations of prior art methods and apparatus. In the following description, and throughout this specification, the expressions "focus", "focusing", and "focused", among others, repeatedly appear, for example, as in "focusing device", "x-ray focusing device", "means for focusing", "focusing optic", among others. Though according to the present invention these expressions can apply to devices or methods in which x-rays are indeed "focused", for example, caused to be concentrated, these expressions are not meant to limit the invention to devices that "focus" x-rays. According to the present invention, the term "focus" and related terms are intended to also serve to identify methods and devices which collect x-rays, collimate x-rays, converge x-rays, diverge x-rays, or devices that in any way vary the intensity, direction, path, or shape of x-rays. All these means of handling, manipulating, varying, modifying, or treating x-rays are encompassed in this specification by the term "focus" and its related terms.

One aspect of the present invention is an x-ray tube assembly comprising: an x-ray tube; and a thermally-conductive, dielectric material thermally coupled to the x-ray tube for removing heat generated by the x-ray tube. The thermally-conductive, dielectric material may be aluminum nitride, beryllium oxide, and diamond-like carbon, among others. The x-ray tube assembly may include an x-ray tube having a first end and a second end, and the first end of the x-ray tube including an electron beam generator and the second end of the x-ray tube including an anode having a surface upon which the electron beam is impinged to generate a source of x-rays. The thermally-conductive, dielectric material is typically thermally coupled to the anode. Cooling means may also be thermally coupled to the thermally-conductive, dielectric material, for example, at least one cooling fin or cooling pin. In one aspect of the invention, sufficient heat may be removed from the x-ray tube by means of the thermally-conductive, dielectric material whereby the x-ray tube assembly may be air cooled. In one aspect of the invention, sufficient heat may be removed from the x-ray tube by means of the thermally-conductive, dielectric material whereby the x-ray tube is not contacted with a fluid coolant.

Another aspect of the invention comprises a method of operating an x-ray tube assembly having an electron beam generator and an anode, comprising: directing a beam of electrons from the electron beam generator to the anode to generate x-rays and thereby heat the anode; providing a thermally-conductive, dielectric material thermally coupled with the anode, and conducting heat from the anode by means of the thermally-conductive, dielectric material. Again, the thermally-conductive, dielectric material may be aluminum nitride, beryllium oxide, or diamond-like carbon, among others. In one aspect, the anode is electrically isolated and little or no electrons pass from the anode to the thermally-conductive, dielectric material. In one aspect of this method, sufficient heat may be removed from the anode when conducting heat from the anode by means of the thermally-conductive, dielectric material whereby the x-ray tube assembly may be air cooled. In one aspect of this method, sufficient heat may be removed from the anode when conducting heat from the anode by means of the thermally-conductive, dielectric material whereby the x-ray tube is not contacted with a fluid coolant.

Another aspect of the invention comprises an x-ray source assembly, comprising: a housing; an x-ray tube for generating x-rays, the x-ray tube being mounted in the housing; a thermally-conductive, dielectric material thermally coupled to the x-ray tube for removing heat generated by the x-ray tube; and at least one perforation in the housing for emitting x-rays generated by the x-ray tube. The x-ray source assembly may further include means for adjustably mounting the x-ray tube in the housing. In one aspect, the x-ray source assembly includes an x-ray tube having a first end and a second end and the first end of the x-ray tube comprises an electron beam generator and the second end of the x-ray tube comprises a surface upon which the electron beam is impinged to generate the x-rays. Again, the thermally-conductive, dielectric material may be aluminum nitride, beryllium oxide, or diamond-like carbon, among others. The dielectric material may also be cooled by at least one cooling fin or cooling pin thermally coupled to the thermally-conductive, dielectric material. The x-ray source assembly may also have an x-ray source which is adjustably mounted to the x-ray tube housing, for example, by at least one threaded pin. The x-ray source assembly may also include means for varying or modifying the x-rays emitted through the at least one perforation in the housing, for example, by means of a moveable baffle with at least one perforation. In one aspect of the invention, an x-ray optic may be mounted to receive at least some x-rays emitted through the at least one perforation in the housing. In one aspect of this assembly, sufficient heat may be removed from the x-ray tube by means of the thermally-conductive, dielectric material whereby the x-ray tube assembly may be air cooled. In one aspect of this assembly, sufficient heat may be removed from the x-ray tube by means of the thermally-conductive, dielectric material whereby the x-ray tube is not contacted with a fluid coolant.

Another aspect of the present invention comprises a method of operating an x-ray tube assembly having a first end comprising an electron beam generator and a second end having an anode and a thermally-conductive, dielectric material thermally coupled with the anode, comprising: directing a beam of electrons from the electron beam generator to the anode to provide x-rays and thereby heat the anode; and cooling the anode by conducting heat from the anode to the thermally-conductive, dielectric material. The x-ray tube assembly may also include at least one cooling pin or cooling fin and cooling the anode may further include passing a fluid coolant over the at least one cooling pin or cooling fin. Also, the cooling of the anode by conducting heat from the anode to the thermally-conductive, dielectric material may be practiced while passing little or no electrons from the anode. In one aspect of this method, sufficient heat may be removed from the anode when cooling the anode by conducting heat from the anode by means of the thermally-conductive, dielectric material whereby the x-ray tube assembly may be air-cooled. In another aspect of this method, sufficient heat may be removed from the anode when cooling the anode by conducting heat from the anode by means of the thermally-conductive, dielectric material whereby the x-ray tube is not contacted with a fluid coolant.

Another aspect of the present invention comprises a method for optimizing transmission of x-rays from an x-ray source and an x-ray focusing device wherein the x-ray source comprises an x-ray tube for generating x-rays, the x-ray tube being mounted in a housing by adjustable mounting means, and the housing having at least one perforation for emitting x-rays generated by the x-ray tube, the method comprising: mounting the x-ray tube in the housing; energizing the x-ray tube whereby a beam of x-rays is emitted through the at least one perforation in the housing; mounting the x-ray focusing device adjacent to the at least one perforation in the housing whereby the x-ray focusing device receives at least some x-rays from the x-ray tube; and adjusting the adjustable mounting means of the x-ray tube to optimize transmission of x-rays through the x-ray focusing device. The adjustable mounting means may comprise a plurality of threaded fasteners. The x-ray focusing device may comprise an x-ray focusing crystal or an x-ray focusing capillary device.

A further aspect of the present invention is an x-ray fluorescence analysis system, comprising: an x-ray source assembly having an x-ray source and a housing; a first x-ray focusing device operatively connected to the x-ray source assembly and having means for aligning the first x-ray focusing device with the x-ray source assembly; an x-ray exposure assembly having a housing operatively connected to the x-ray focusing device and having means for aligning the x-ray exposure assembly with the first x-ray focusing device; a second x-ray focusing device operatively connected to the x-ray exposure assembly and having means for aligning the second x-ray focusing device with the x-ray exposure assembly; and an x-ray detection device operatively connected to the second x-ray focusing device and having means for aligning the x-ray detection device with the second x-ray focusing device; wherein at least one of the means for aligning comprises a plurality of alignment pins. The alignment of at least one of the assemblies, preferably a plurality of assemblies, permits one or more of the assemblies to be assembled off site and installed on site without requiring extensive realignment of the assemblies on site. Avoiding realignment on site is more efficient.

Another aspect of the present invention is a method of detecting x-rays, comprising: providing a source of x-rays; focusing at least some of the x-rays using an x-ray optic on a small-area x-ray detector; and detecting the x-rays by means of the small-area x-ray detector. In one aspect of the invention, the small-area detector may be may be a semiconductor-type detector or a silicon-lithium-type detector (that is, a SiLi-type detector). In one aspect of the invention, the small-are detector may be a PIN-diode-type detector. One aspect of the invention further comprises cooling the small-area detector, for example, air-cooling the small-area detector. The small-area ray detector may include a detector aperture and the detector aperture area may be less than about 10 square millimeters, preferably, less than about 6 square millimeters, or even less than about 4 square millimeters. The focusing of at least some of the x-rays may be practiced using a capillary-type x-ray optic or a DCC x-ray optic. The method may be practiced at a temperature greater than about 0 degrees centigrade, for example, at a temperature between about 10 degrees centigrade and about 40 degrees centigrade.

A further aspect of the invention comprises a device for detecting x-rays, comprising: a small-area x-ray detector; and means for focusing at least some of the x-rays on small-area x-ray detector. The small-area x-ray detector typically includes a detector aperture having an area less than about 10 square millimeters, typically, less than about 6 square millimeters. The small-area x-ray detector may be a semiconductor-type detector or a silicon-lithium-type detector. In one aspect of the invention the small-area detector may be a PIN-diode-type. In one aspect of the invention, the small-area detector may be cooled, for example, air-cooled. The means for focusing at least some x-rays may comprise an x-ray optic, for example, a curved-crystal or capillary x-ray optic.

Another aspect of the invention comprises an apparatus for analyzing a fluid using x-rays, comprising: means for exposing the fluid to x-rays to cause at least one component of the fluid to x-ray fluoresce; and means for analyzing the x-ray fluorescence from the fluid to determine at least one characteristic of the fluid. The fluid may be a liquid or a gas. The means for exposing the fluid to x-rays may be at least one x-ray optic for focusing x-rays on the fluid.

Another aspect of the present invention comprises a method for analyzing components in a fluid using x-rays, comprising: exposing the fluid to x-rays to cause at least one component in the fluid to x-ray fluoresce; detecting the x-ray fluorescence from the fluid; and analyzing the detected x-ray fluorescence to determine at least one characteristic of the fluid. According to one aspect, the method is practiced essentially continually for a period of time. The method may also be practiced under vacuum.

In one aspect, the detecting of the x-ray fluorescence is practiced at a temperature greater than about minus 50 degrees centigrade, for example, at greater than about 0 degrees centigrade. In another aspect of the method, the detecting of the x-ray fluorescence may be practiced using a small-area x-ray detector, for instance, a semiconductor-type x-ray detector, for example, a PIN-type semiconductor x-ray detector.

Another aspect of the present invention comprises an apparatus for analyzing sulfur in a fuel, comprising: means for exposing the fuel to x-rays to cause at least some sulfur in the fuel to x-ray fluoresce; and means for analyzing the x-ray fluorescence from the fuel to determine at least one characteristic of the sulfur in the fuel. The at least one characteristic of the sulfur in the fuel may be the concentration of sulfur in the fuel.

A still further aspect of the present invention is a method for analyzing sulfur in a fuel, comprising: exposing the fuel to x-rays to cause at least some of the sulfur in the fuel to x-ray fluoresce; detecting the x-ray fluorescence; and analyzing the x-ray fluorescence from the sulfur to determine at least one characteristic of the sulfur in the fuel. The method is typically practiced essentially continually for a period of time. The exposing of the fuel to x-rays may be practiced under vacuum. When practiced under vacuum, the fuel will typically be enclosed in a chamber to prevent exposure to the vacuum, for example, the fuel may be enclosed in a chamber and the x-rays access the fuel via a window in the chamber. According to one aspect, the x-rays may be monochromatic x-rays. Also, the detecting of the x-ray fluorescence may be practiced at a temperature greater than about minus 100 degrees centigrade, typically greater than about minus 50 degrees centigrade, or even greater than about 0 degrees centigrade, for example at about room temperature (20 degrees centigrade). The detecting may be practiced using a semiconductor-type detector, for example, a PIN-type semiconductor detector.

Regarding improved heat dissipating aspects of the invention, the invention is a device for cooling and electrically-insulating a high-voltage, heat-generating component. This device includes: a first thermally-conductive material having a first side in thermal communication with the component and a second side; a thermally-conductive dielectric material having a first side in thermal communication with the second side of the first thermally-conductive material and a second side; and a second thermally-conductive material having a first side in thermal communication with the second side of the thermally-conductive, dielectric material; wherein heat generated by the component is conducted away from the component through the device while current loss across the device is minimized. In one aspect of the invention, the thermal communication between the component and the first thermally-conductive material is through an area of contact between the component and the first thermally-conductive material, the area of contact having a first outer dimension, and wherein the first thermally-conductive material comprises a periphery having a second outer dimension, greater than the first outer dimension, wherein at least some heat from the component is conducted in the first thermally-conductive material in a direction from the area of contact toward the periphery of the first thermally-conductive material. In another aspect of the invention, the first thermally-conductive material comprises a first plate, wherein at least some heat is conducted in the first plate in a direction from the area of contact toward the periphery of the first plate, and hence through the thermally-conductive dielectric material to the second thermally-conductive material. The invention may also include means for facilitating removal of heat from the second thermally-conductive material, for example, at least one cooling fin or cooling pin. In one aspect of the invention, the thermally-conductive dielectric material comprises one of aluminum nitride, beryllium oxide, and diamond-like carbon. The high-voltage, heat-generating component may be an x-ray generator, an electron-beam generator, a high-voltage lead, or a microwave generator, among other devices.

This aspect of the invention may be used with the fluid-analyzing technique and optics discussed above.

Another aspect of the heat dissipating invention is an x-ray tube assembly including: an x-ray tube comprising a high-voltage, heated anode; and a heat dissipating device coupled to the anode, the heat dissipating device comprising: a first metal plate having a first side in thermal communication with the anode and a second side; a thermally-conductive dielectric material plate having a first side in thermal communication with the second side of the first metal plate and a second side; and a second metal plate having a first side in thermal communication with the second side of the thermally-conductive dielectric material plate; wherein heat generated in the anode is conducted away from the anode through the device while current loss across the device is minimized. In one enhanced aspect of the invention, the heat dissipating device provided structural support for the anode, for example, the heat dissipating device can provide essentially all the structural support for the anode. In another aspect of the invention, the x-ray tube assembly further includes a high voltage connector coupled with the first metal plate.

This aspect of the invention may be used with the fluid-analyzing technique and optics discussed above.

A further aspect of the heat dissipation invention is a method for fabricating a device for cooling and electrically-insulating a high-voltage, heat-generating component, the method comprising: providing a first thermally-conductive material having a first surface for contacting the component and a second surface; providing a thermally-conductive dielectric material having a first surface and a second surface; coupling the first surface of the first thermally-conductive dielectric material to the second surface of the first thermally-conductive material, so that the first thermally-conductive material and the thermally-conductive dielectric material are in thermal communication; providing a second thermally-conductive material having a first surface and a second surface; and coupling the first surface of the second thermally-conductive material to the second surface of the thermally-conductive dielectric material so that the thermally-conductive dielectric material and the second thermally-conductive material are in thermal communication. In one aspect of the invention, coupling comprises, gluing, adhesive bonding, soldering, brazing, or welding. One adhesive that may be used is Dow Chemical's 4174 thermally-conductive, silicone adhesive, or its equivalent. Another aspect of the invention further includes coupling a high voltage connector to the electrically-conductive, first thermally-conductive material.

This aspect of the invention may be used with the fluid-analyzing system and optics discussed above.

Since it may be desirable to align the x-ray beam produced by an x-ray device with an internal or external x-ray optic, according to one aspect of the invention, the components of an x-ray beam device are mounted in-a way that enables the user to adjust the position or direction of the x-ray beam relative to an optic to account for, among other things, variations in alignment due to thermal expansion. Furthermore, since the alignment of an x-ray beam device with an optic can be difficult when the x-ray tube is bolted inside a sealed container and the sealed container contains a cooling fluid, in one aspect of the invention, x-ray beam device is provided which requires little or no cooling fluid. For example, according to one aspect of the invention, an x-ray beam device is provided having sufficient cooling yet permitting alignment of the device, for example, precise alignment with an optical device.

This aspect of the invention may be used with the fluid-analyzing system and optics discussed above.

Regarding the enhanced stability aspects of the invention, the use of e-beam impingement upon an anode to generate x-rays, such as in the x-ray tubes described above, can generate an amount of heat that is sufficient to cause thermal expansion of the elements which support and position the x-ray tube within the x-ray source. This thermal expansion can be sufficient to cause a misalignment between the x-rays that are diverging from the anode and, e.g., the element that serves to control the direction of the x-rays. As a result, operating an x-ray source at different powers may lead to a range of misalignments between the diverging x-rays and the focusing electrode. This misalignment could cause the output power intensity of the x-ray source to vary widely. Misalignment could also cause changes in x-ray spot or x-ray beam position for some types of beam controlling elements, e.g., for pinholes or single reflection mirrors. Thus, in one aspect, provided herein is an x-ray source assembly having enhanced output stability over a range of operating power levels, as well as enhanced x-ray spot or x-ray beam position stability. More particularly, an x-ray source assembly in accordance with an aspect of the present invention provides an x-ray beam output intensity which can be maintained relatively constant notwithstanding variation in one or more operating conditions of the x-ray source, such as anode power level, housing temperature and ambient temperature about the assembly.

This aspect of the invention may be used with the fluid-analyzing system, optics and heat dissipation aspects discussed above.

For enhanced stability, additional advantages are provided through the provision of an x-ray source assembly which includes an anode having a source spot upon which electrons impinge, and a control system for controlling position of the anode source spot relative to an output structure. The control system can maintain the anode source spot location relative to the output structure notwithstanding a change in one or more operating conditions of the x-ray source assembly.

This aspect of the invention may be used with the fluid-analyzing system, optics and heat dissipation aspects discussed above.

In another enhanced stability aspect of the invention, an x-ray source assembly is provided which includes an x-ray tube having an anode for generating x-rays, and an optic for collecting x-rays generated by the anode. The x-ray source assembly further includes a control system for controlling x-ray output intensity of the optic. The control system can maintain x-ray output intensity notwithstanding a change in one or more operating conditions of the x-ray source assembly.

This aspect of the invention may be used with the fluid-analyzing system, optics and heat dissipation aspects discussed above.

In still another enhanced stability aspect of the invention, a method of providing x-rays is presented which includes: providing an x-ray source assembly having an anode with a source spot upon which electrons impinge; and controlling position of the anode source spot relative to an output structure, wherein the controlling includes maintaining the anode source spot location relative to the output structure notwithstanding a change in at least one operating condition of the x-ray source assembly.

This aspect of the invention may be used with the fluid-analyzing system, optics and heat dissipation aspects discussed above.

In a further enhanced stability aspect of the invention, a method of providing x-rays is presented which includes: providing an x-ray source assembly having an x-ray tube with an anode for generating x-rays and an optic for collecting x-rays generated by the anode; and controlling x-ray output intensity from the optic, wherein the controlling includes maintaining x-ray output intensity from the optic notwithstanding a change in at least one operating condition of the x-ray source assembly.

This aspect of the invention may be used with the fluid-analyzing system, optics and heat dissipation aspects discussed above.

These and other embodiments and aspects of the present invention will become more apparent upon review of the attached drawings, description below, and attached claims.

BRIEF DESCRIPTION OF THE DRAWINGS

The subject matter which is regarded as the invention is particularly pointed out and distinctly claimed in the concluding portion of the specification. The invention, however, both as to organization and method of practice, together with further objects and advantages thereof, may best be understood by reference to the following detailed descriptions of the preferred embodiments and the accompanying drawings in which:

FIG. 18 depicts a cross-sectional view of one embodiment of an enhanced x-ray source assembly, in accordance with an aspect of the present invention;

FIG. 21 is an exemplary reference temperature table which can be employed by the control processing of FIG. 20, in accordance with an aspect of the present invention.

DETAILED DESCRIPTION OF THE PREFERRED EMBODIMENTS

Figure 1:
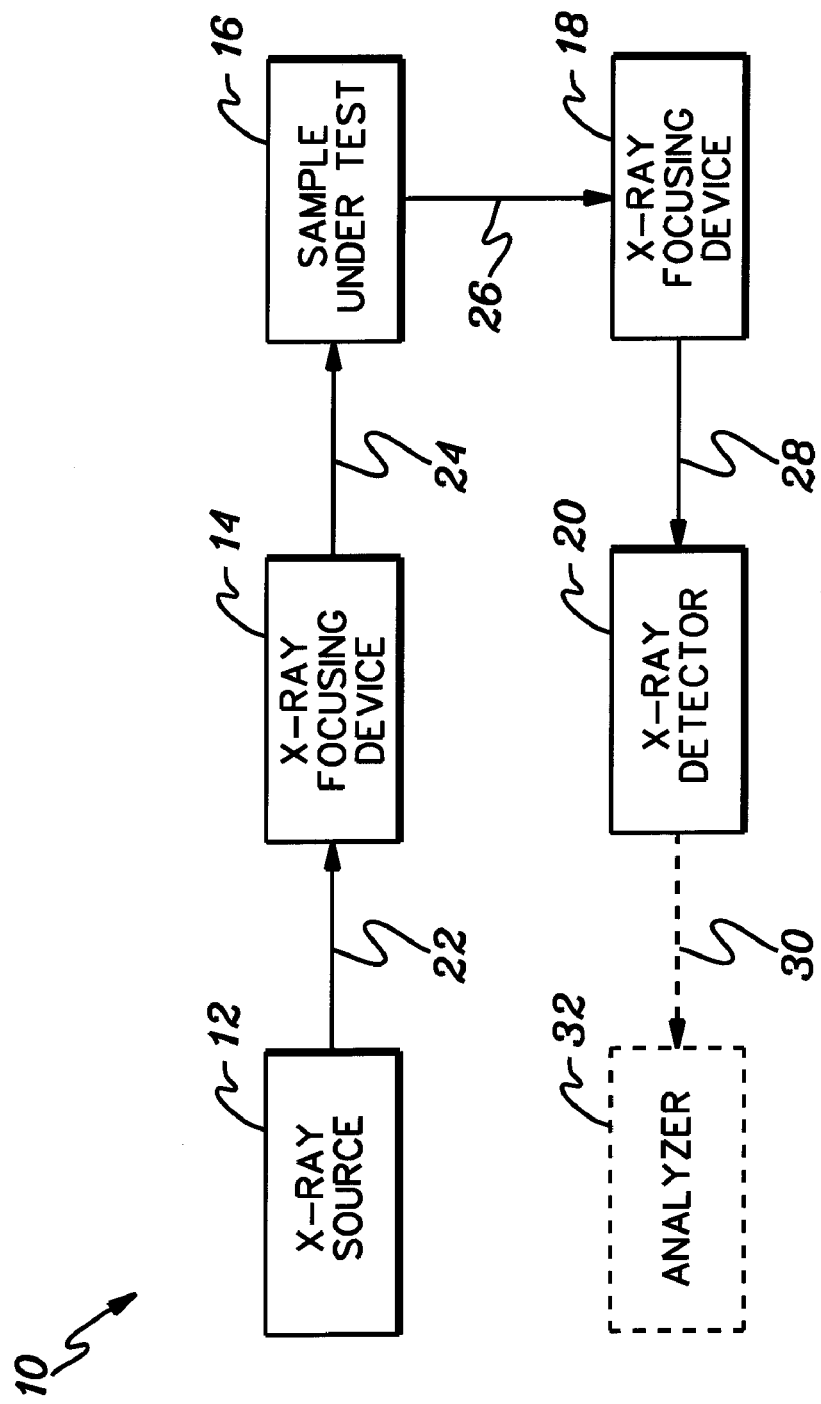
FIG. 1 is a schematic block diagram of an x-ray fluorescence system that can be used to practice the present invention.

FIG. 1 illustrates a schematic block diagram of a typical system 10 used for exposing a substance to x-ray radiation to produce flourescent radiation which can then be detected and analyzed to determine a characteristic of the substance. Such a system typically includes an x-ray source 12, a first x-ray focusing device 14, a sample excitation chamber 16, a second x-ray focusing device 18, and an x-ray detector 20. The x-ray source 12, for example, an x-ray tube, produces a beam of x-rays 22. Since x-ray beam 22 is typically a divergent beam, beam 22 is diffracted or focused by means of one or more x-ray focusing devices 14. X-ray focusing device 14 may be one or more doubly-curved crystals, for example, a doubly-curved crystal having essentially parallel atomic planes, such as the crystals disclosed in pending application Ser. No. 09/667,966 filed on Sep. 22, 2000, the disclosure of which is incorporated by reference herein. X-ray focusing device may be one or more capillary-type x-ray optic or curved crystal optic, for example, one of the optics disclosed in U.S. Pat. Nos. 6,317,483; 6,285,506; 5,747,821; 5,745,547; 5,604,353; 5,570,408; 5,553,105; 5,497,008; 5,192,869; and 5,175,755, the disclosures of which are incorporated by reference herein. The one or more x-ray focusing devices produces a focused beam 24 directed toward the sample excitation chamber 16.

The sample under test in excitation chamber 16 may be any desired substance for which a characteristic is desired. The sample may be a solid, a liquid or a gas. If the sample is a solid, the sample is typically located on a relatively flat surface, for example, an x-ray reflective flat surface, for example, an optically-reflective surface. The sample, if a solid, liquid, or gas, may also be contained in a closed container or chamber, for example, a sealed container, having a x-ray transparent aperture through which x-ray beam can pass. When irradiated by beam 24, at least one of the constituents of sample in chamber 16 typically is excited in such a fashion that the constituent x-ray fluoresces, that is, produces a secondary source of x-rays 26 due to excitation by x-rays 24. Again, since x-ray beam 26 is typically a diverging beam of x-rays, beam 26 is focused by means of the second x-ray focusing device 18, for example, a device similar to device 14, to produce a focused beam of x-rays 28 directed toward x-ray detector 20. It will be apparent to those of skill in the art that this and other aspects of the present invention, though described with respect to x-ray fluorescence applications, may also be utilized in x-ray absorption applications.

X-ray detector 20 may be a proportional counter-type or a semiconductor type x-ray detector. Typically, x-ray detector 20 produces an electrical signal 30 containing at least some characteristic of the detected x-rays which is forwarded to an analyzer 32 for analysis, printout, or other display.

Figure 2:
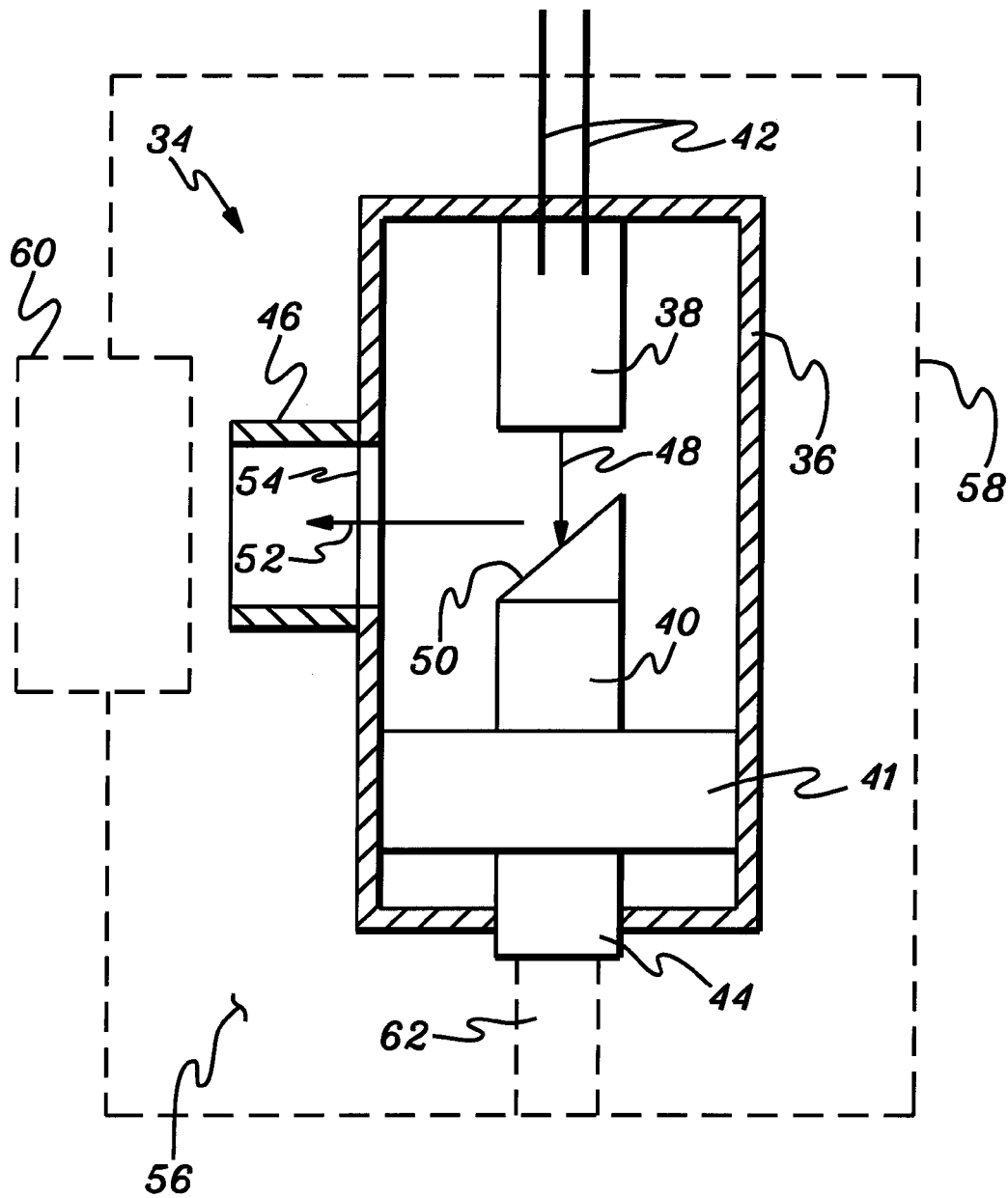
FIG. 2 is a schematic cross-sectional view of a prior art x-ray tube over which one aspect of the present invention is an improvement.

Various aspects of the present invention provide advancements and improvements to the system 10 and system components shown in FIG. 1. One of these aspects of the present invention is disclosed with respect to FIGS. 2 and 3. FIG. 2 illustrates a cross-section of a typical prior art x-ray tube assembly 34, for example, a Series 5000 TF5011 x-ray tube produced by Oxford Instruments of Scotts Valley, Calif., though other similar x-ray tubes may be used. As is typical, this prior art x-ray tube 34 includes a cylindrical housing 36, which typically comprises a non-conducting glass housing. An electron-beam generator 38 and an anode 40 are mounted in housing 34 typically in the orientation shown. Anode 40 is typically a thin solid material, for example, tungsten or Chromium mounted on a conducting anode of copper or a similar high-thermal-conductivity material. Anode 40 is typically fashioned to provide surface 50 and having cylindrical support structure 41 fashioned to provide a rigid support for anode 40 in housing 41 and also to isolate the gas volume above structure 41 from the volume below structure 41. Anode 40 also includes a cylindrical non-conducting support 44 which penetrates housing 36. Electrical connections 42 provide power to the electron-beam generator 38. Housing 36 typically includes at least one aperture 46 for emitting the x-rays produced by x-ray tube 34. Housing 36 typically isolates the internal volume of tube 34 from the ambient environment and the internal volume of tube 34 is typically provided with at least some form or vacuum, for example, about $10^{-6}$ Torr.

When power, for example, 50 Watts, is provided to electrical connections 42, electron-beam generator 38 produces a beam of electrons, as indicated by arrow 48, directed towards surface 50 of anode 40. Surface 50 is typically an inclined surface, for example, inclined at about 45 degrees to the axis of the tube. The interaction of electron beam 48 with surface 50 produces x-rays which are scattered in all directions. The wavelength and frequency of the x-rays produced is a function of the power provided to electrical connections 42, among other things. However, at least one path of these scattered x-rays is indicated by arrow 52 directed toward aperture 46. The direction of x-ray beam 52 is a typically a function of the orientation of tube 34. The x-ray beam represented by arrow 52 passes through x-ray permeable barrier 54 in aperture 46. The x-ray permeable barrier 54 is typically made from beryllium (Be) or titanium (Ti) which permits the passage of x-rays while isolating the internal volume of the housing 36 from the ambient environment.

The generation of x-rays by the impingement of electron beam 48 upon anode 40 generates substantial heat, for example, the temperature of anode 40 typically is elevated to a least 60 degrees centigrade, and can reach as high as the melting point of tungsten. In consequence, tube 34 is typically immersed in a cooling and insulating fluid 56, for example, an petroleum-based oil. Tube 34 and fluid 56 are typically contained in a cylindrical housing 58. Housing 58 is typically impermeable to x-rays, for example, housing 58 can be typically lead-lined. The volume of cooling and insulating fluid 56 and thus the size of housing 58 is a function of the cooling requirements of x-ray tube 34. Housing 58 also typically includes an aperture 60 aligned with aperture 46 of tube 34 to emit x-rays generated by tube 34. Tube 34 is typically rigidly mounted within housing 58 by means of a supporting structure 62 attached to support 44 of tube 34, for example, by means of a threaded connection.

Support 44 is typically made of a non-conducting material, for example, a ceramic material, to electrically isolate anode 40 from housing 58.

Figure 3:
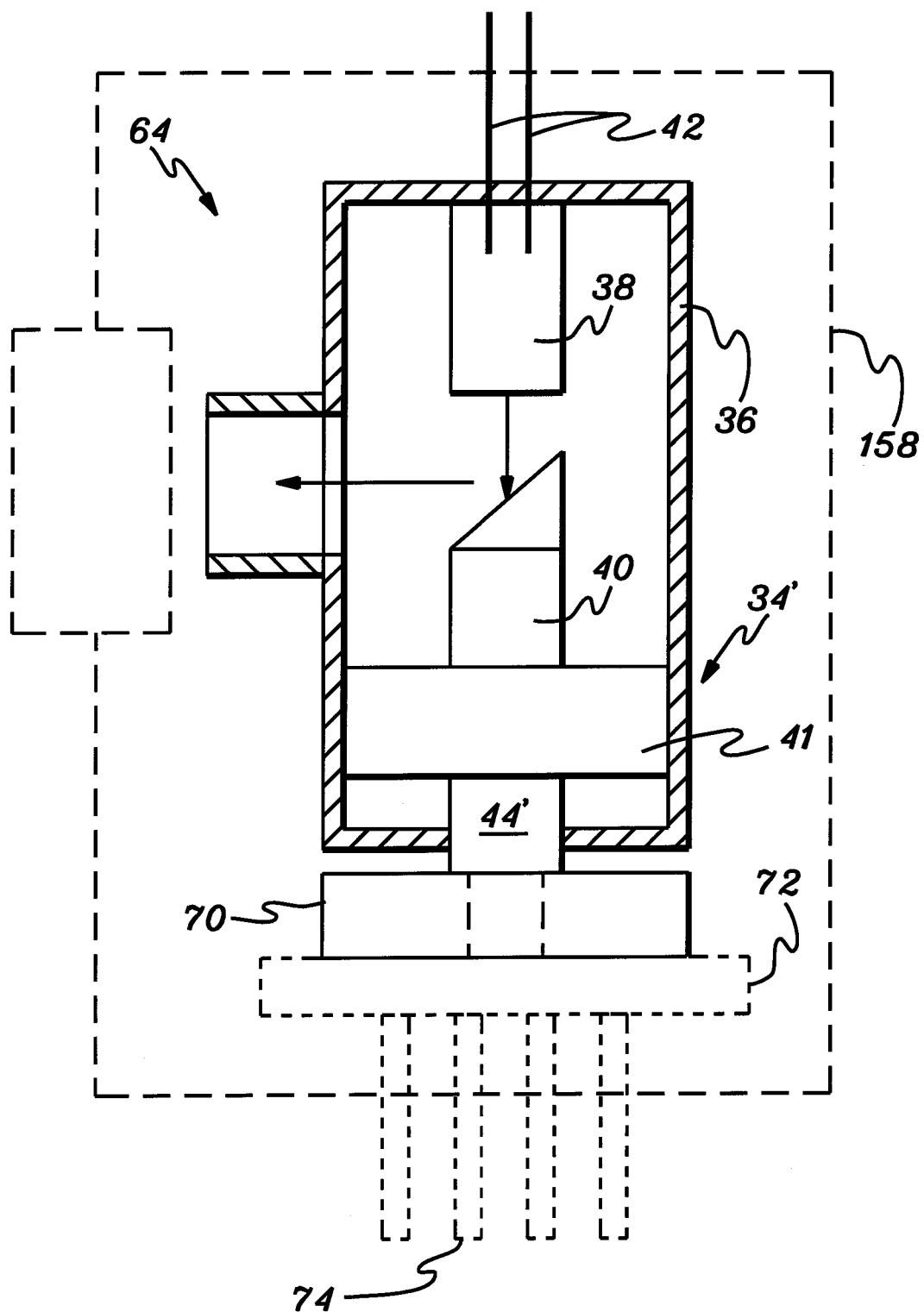
FIG. 3 is a schematic cross-sectional view of one aspect of the present invention.

FIG. 3 illustrates an x-ray tube assembly 64 according to one aspect of the present invention that is an improvement over the prior art x-ray tube assembly illustrated in FIG. 2. Many of the features that appear in FIG. 3 can be essentially identical to the features of FIG. 2 and are identified with the same reference numbers. According to this aspect of the present invention, x-ray tube assembly 64 includes an x-ray tube 34' (which may be similar to tube 34) having a housing 36, an electron-beam generator 38, an anode 40, and an aperture 46 essentially identical to the structures illustrated and described with respect to FIG. 2. However, according to the present invention, x-ray tube assembly 64 includes at least one thermally-conducting, but non-electrically conducting material 70 mounted or thermally coupled to x-ray tube 34'. The thermally-conducting, non-electrically conducting material (which may be referred to as a thermally-conducting, dielectric material) 70 is a material having a high thermal conductivity and also a high dielectric strength. For example, material 70 typically has a thermal conductivity of at least about 100 $Wm^{-1}K^{-1}$, and preferably at least 150 $Wm^{-1}K^{-1}$; and material 70 typically has a dielectric strength of at least about $1.6 \times 10^7 Vm^{-1}$, preferably at least about $2.56 \times 10^7 Vm^{-1}$. Material 70 may be aluminum nitride, beryllium oxide, diamond-like carbon, a combination thereof, or equivalents or derivatives thereof, among others. In FIG. 3, material 70 is illustrated as a cylindrical structure, for example, a circular cylindrical or rectangular cylindrical structure, though material 70 may take many difference geometrical shapes and provide the desired function.

X-ray tube 64 may typically mounted in a housing 158. Housing 158, like housing 58 in FIG. 2 is typically fabricated from an x-ray impermeable material, for example, a lead-lined material, lead, or tungsten. Housing 158 may assume any appropriate shape, including circular cylindrical and rectangular cylindrical. In one aspect of the invention, housing 158 is fabricated from tungsten plate, and due to the poor machinability of tungsten, housing 158 is preferably rectangular cylindrical in shape. Of course, should methods be produced for providing other means of fabricating tungsten housings, these can also be applied to the present invention.

According to the present invention, thermally-conducting, dielectric material 70 permits the conducting of heat away from anode 40 specifically and tube 34' in general while minimizing or preventing the passage of electrical current from anode 40 specifically and tube 34' in general. In this aspect of the invention, support 44' (unlike support 44 of tube 34 of FIG. 2) is typically made of a conducting material, for example, copper or aluminum. According to this aspect of the invention, heat is conducted away from anode 40 via support 44' and material 70 while material 70 electrically isolates anode 40 from, for example, an external housing 158.

Unlike prior art x-ray tube assemblies, the temperature of x-ray tube 34' according to this aspect of present invention can be reduced by conducting heat away from anode 40 and dissipating the heat to the adjacent environment via the surface area of material 70. Thus, material 70 cools anode 40 specifically and tube 34' in general such that the cooling requirements for tube 34' are reduced, or increased heating of anode 40 can be achieved. For example, in one aspect of the invention, the presence of material 70 provides sufficient means for cooling tube 34' whereby little or no additional cooling means is required. In another aspect of the invention, the presence of material 70 provides sufficient means for cooling tube 34' whereby air cooling provides sufficient cooling of tube 34', for example, forced air cooling (though non-forced-air cooling characterizes one aspect of the invention). In another aspect of the invention, the presence of material 70 provides sufficient means for cooling tube 34' whereby less cooling and insulating fluid is required than the fluid required for prior art x-ray tube assemblies, for example, at least 10% less cooling fluid than prior art tube assemblies; typically, at least 20% less cooling fluid than prior art tube assemblies; preferably, at least 50% less cooling fluid than prior art tube assemblies.

According to one aspect of the present invention, the cooling capacity of material 70 is increased by increasing the surface area of material 70, for example, by means of introducing cooling fins or cooling pins to material 70. In another aspect of the invention, additional cooling capacity is obtained by introducing cooling fins or cooling pins to a structure thermally coupled to material 70. One such optional structure is illustrated in phantom in FIG. 3. FIG. 3 includes plate 72 mounted or otherwise thermally coupled to material 70. Plate 72, made of a thermally conductive material, for example copper or aluminum, may provide sufficient surface area for cooling. In this aspect of the invention, the surface area of the thermally-coupled structure is enhanced by the use of cooling pins or cooling fins 74. According to one aspect of the invention, plate 72 and fins 74 are comprised of a material that is thermally conductive so that heat can be conducted away from material 70, for example, a copper-, iron-, or aluminum-based. In another aspect of the invention, plate 72 is fabricated from a material that is both thermally conductive and resistant to the penetration of x-rays, for example, tungsten-copper. The copper in tungsten-copper provides the conductivity desired while the tungsten provides the desired x-ray shielding. Other materials having the same or similar properties may be used for plate 72. When plate 72 is a duplex material like tungsten-copper, fins 70 may be simply a copper- or aluminum-based material.

Figure 4:
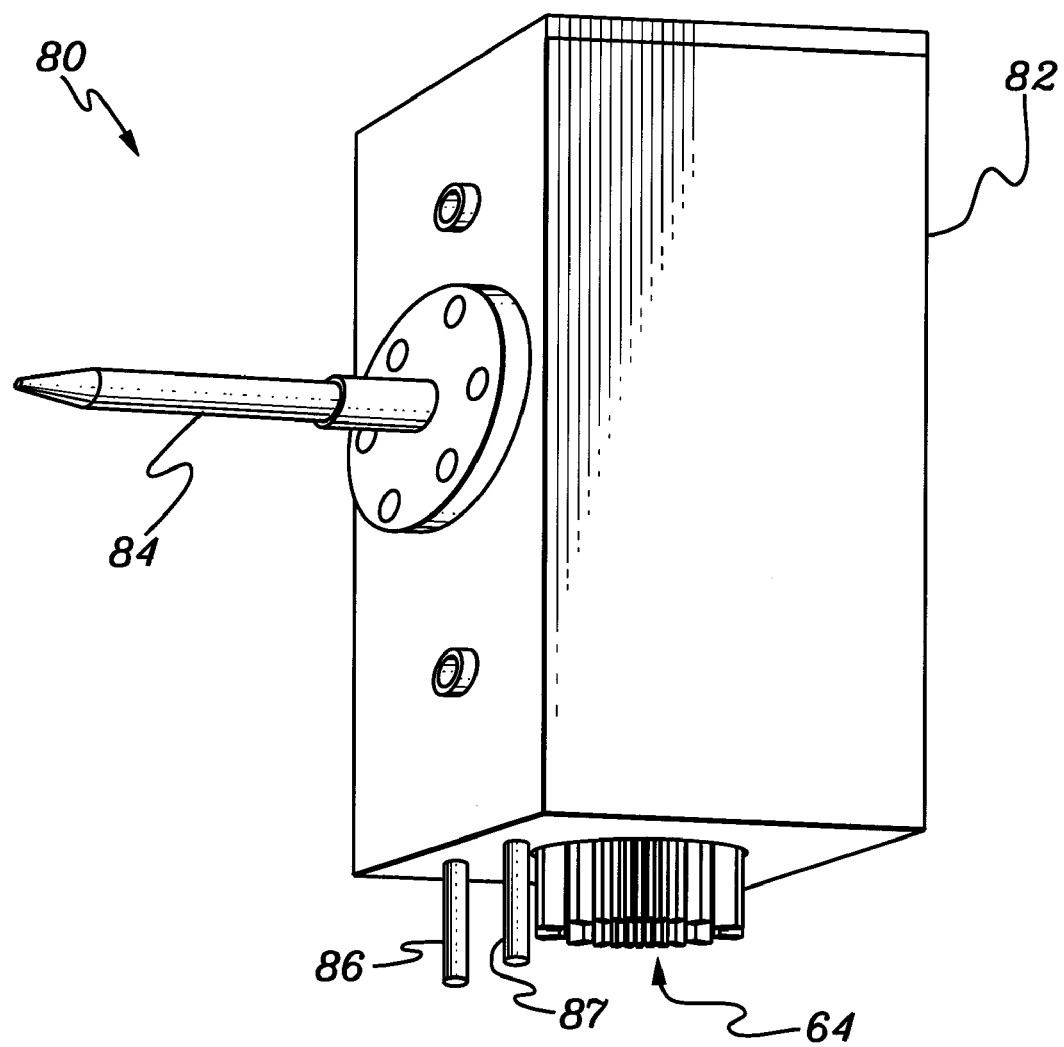
FIGS. 4, 5, and 6 illustrate various perspective views of another aspect of the present invention.
Figure 5:
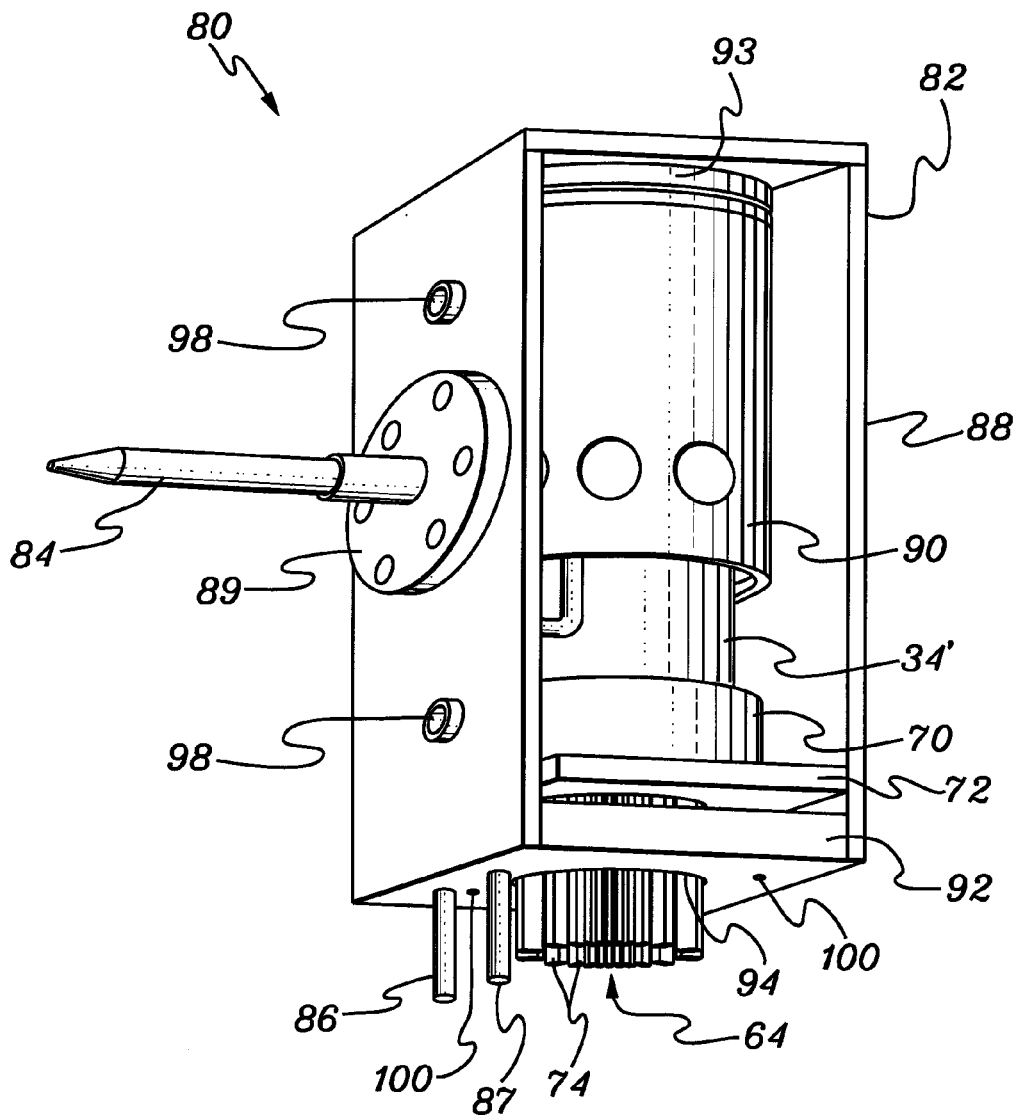
Figure 6:
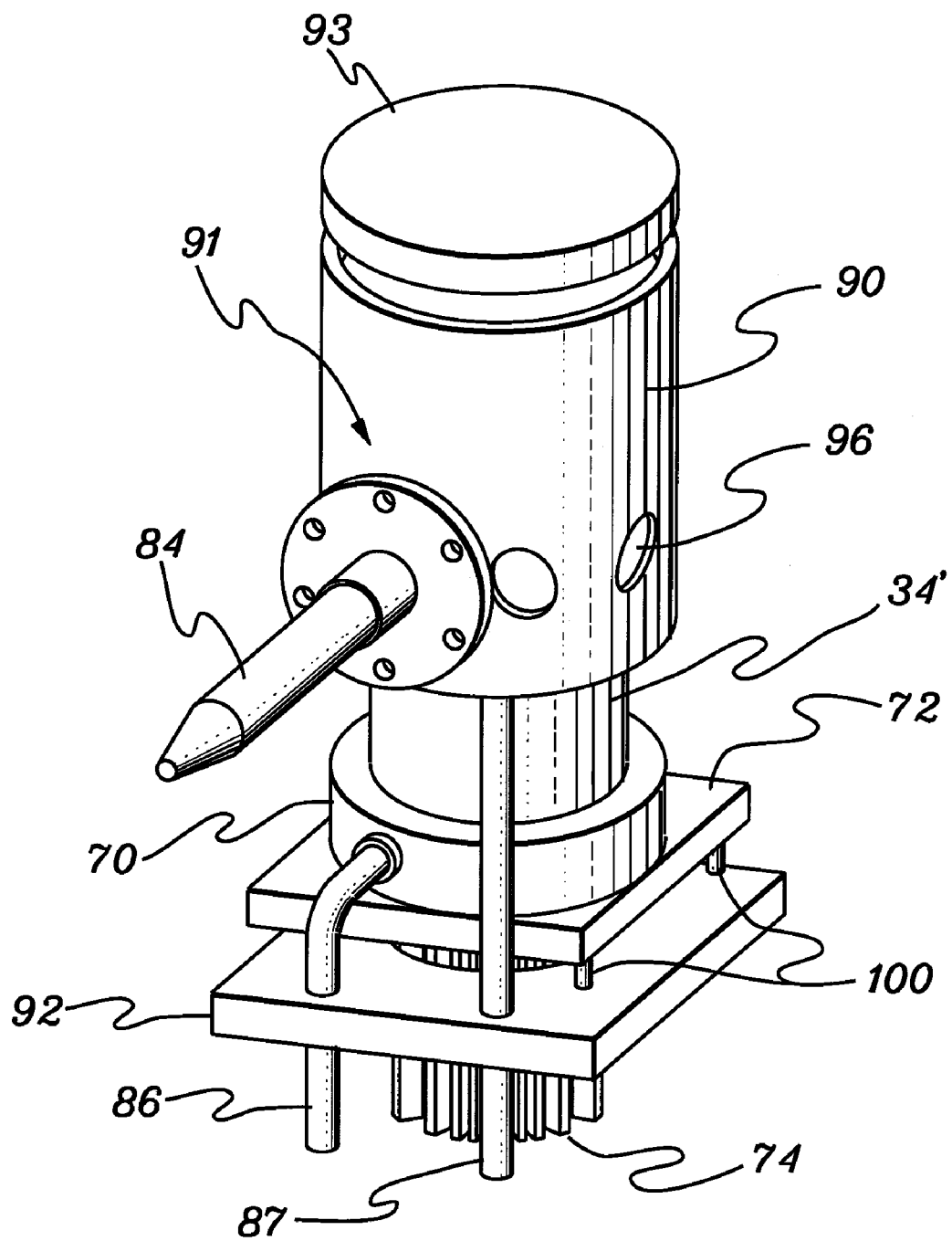

FIGS. 4, 5, and 6 illustrate an x-ray source and x-ray focusing device assembly 80 and an x-ray source assembly 82 according to other aspects of the present invention. X-ray source and x-ray focusing device assembly 80 comprises x-ray source assembly 82 and x-ray focusing device 84. The x-ray focusing device 84 shown in FIG. 4 is a polycapillary x-ray optic as disclosed in above-referenced U.S. patents, but device 84 may be any type of x-ray focusing device, for example, the x-ray focusing crystals and capillary type optics discussed above. In one aspect of the invention x-ray source assembly 82 comprises at least one x-ray source 64 having a thermally-conductive dielectric material 70 as described and illustrated in FIG. 3. Though x-ray source assembly 82 is shown rectangular cylindrical in shape in FIG. 3, assembly 82 may take any convenient geometric shape, including circular cylindrical or spherical. Assembly 82 receives electrical power via electrical connections 86, 87.

FIG. 5 illustrates a cut-away view of x-ray source and x-ray focusing device assembly 80 shown in FIG. 4. As shown in FIG. 5, assembly 80 includes x-ray source assembly 82 and x-ray focusing device 84. X-ray source assembly 82 includes a housing 88, an x-ray tube assembly 64 (as shown in FIG. 3) and an x-ray baffle assembly 90. According to this aspect of the invention, housing 88 is cylindrical in shape, for example, circular or rectangular cylindrical in shape, and fabricated from a x-ray shielding material, for example, lead, a lead-lined material, tungsten, depleted uranium, or combinations thereof. Housing 88 includes at least one perforation (not shown) for emitting x-rays generated by x-ray tube 34' and means 89 for mounting x-ray optic 84. In the aspect of the invention shown in FIG. 5, mounting means 89 comprises a bolted flange connection positioned about the penetration in the housing through which the x-rays generated by x-ray tube 34' pass to optic 84.

Housing 82 may also include a bottom plate 92 having a perforation 94 through which x-ray tube assembly 64 may extend. For example, as shown in FIG. 5, the cooling fins 74 of x-ray tube assembly 64 may extend through bottom plate perforation 94, for example, to provide air access to cooling fins 74. As shown, in one aspect of the invention cooling fins 74 may be radially directed.

According to another aspect of the present invention, housing 88 preferably includes at least one means of aligning housing 88 to the components to which it is mounted. For example, the aligning means in housing 88 may include one or more dowel pins or dowel pin holes 98 that are referenced to the orientation of the x-ray tube source spot. The adjustment and orientation of these dowel holes or pins will be discussed below.

X-ray source assembly 82 may also include a baffle plate assembly 90 for varying the amount and type of x-rays emitted from assembly 82. According to this aspect of the invention, baffle assembly 90 includes a baffle cylinder 91 having at least one penetration 96, preferably a plurality of penetrations 96, which are translatable relative to the x-ray aperture in the x-ray tube assembly, for example, relative to aperture 46 shown in FIG. 3. Apertures 96 may vary in size and shape or may contain one or more x-ray filtering devices that can be used to vary the amount and type of x-rays emitted by assembly 82. Though baffle assembly 90 may comprise any type of plate having one or more apertures, according to the aspect of the invention shown in FIG. 5, baffle assembly 90 comprises a circular cylinder 91 mounted about the axis of x-ray tube 34' and rotatably mounted to housing 88. Baffle cylinder 91 may be mounted on disk 93. According to this aspect of the present invention, the orientation of apertures 96 relative to the aperture of tube 34' (again see FIG. 3) may be varied by rotating baffle cylinder 91 via disk 93 by means not shown. The means of rotating baffle cylinder 91 may be manual means or automated means, for example, by means of a stepper motor or linear actuator.

FIG. 6 illustrates a view of x-ray source and focusing device assembly 80 of FIGS. 4 and 5 with the sides and top of housing 88 removed for clarity of illustration. FIG. 6 illustrates x-ray tube assembly 64, baffle cylinder assembly 90, and x-ray optic 84. FIG. 6 also illustrates the adjustable mounting of x-ray tube assembly 64 onto the bottom plate 92 of housing 88. As shown in FIG. 5, electrical connection 86 is operatively connected to anode 40 of tube 34' and electrical connection 87 is operatively connected to electron-beam anode generator 38 of tube 34' (see FIG. 3).

According to this aspect of the invention, x-ray tube assembly 64 (having thermal conductive, dielectric material 70) is adjustably mounted to housing 88 whereby the direction and orientation of the x-rays emitted by x-ray tube 34' may be varied and optimized, for example, optimized for alignment with x-ray optic 84. Though many means of varying the orientation and alignment of x-ray tube assembly 64 may be used, including rotational and transnational adjustment, according to the aspect of the invention shown in FIGS. 4, 5, and 6, orientation and alignment of x-ray tube assembly 64 is effected by means of at least one threaded rod or screw, preferably a plurality of threaded rods or screws. In the aspect shown in FIG. 6, three threaded screws 100 are threaded through bottom plate 92 and engage the bottom surface of plate 72. Screws 100 may be threaded into holes, for example threaded holes in plate 72, or may simply bear against the bottom surface of plate 72. The adjustment of screws 100 or any other means of adjustment may be practiced manually or may be automated.

According to one aspect of the invention, the adjustment of the orientation or tube assembly 64 is registerable with the housing 88. That is, in one aspect of the invention, the orientation of the x-ray beam produced by x-ray tube 34' is registerable to housing 88 and the alignment of components mating to x-ray source assembly 82. For example, x-ray focusing devices or sample excitation chamber, may be aligned to x-ray tube 34' by simply aligning with one or more datum points on the housing. In the aspect of the invention shown in FIGS. 4, 5, and 6, the orientation and alignment of the x-ray beam created by x-ray tube 34' is registered with the one or more dowel pins or dowel pin holes 98 on housing 88. As a result, by appropriately aligning mating components to dowel pins or holes 98, mating components can be accordingly aligned with the x-ray beam of tube 34', for example, with little or no further adjustment.

Figure 7:
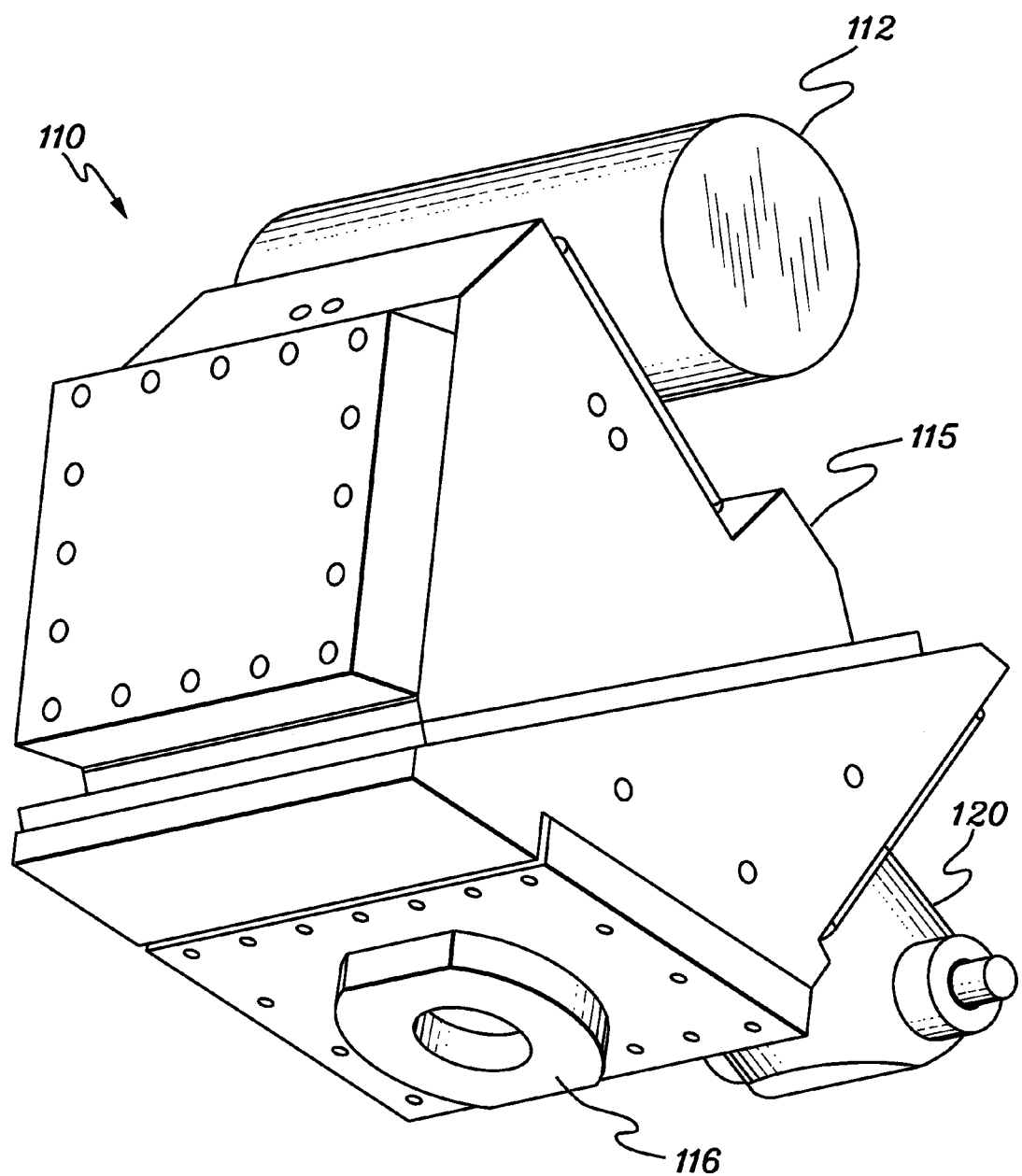
FIG. 7 is a perspective view of the housing assembly of another aspect of the present invention.

FIG. 7 illustrates an x-ray fluorescence assembly 110 according to another aspect of this invention. X-ray fluorescence assembly 110 comprises an x-ray source assembly 112, a sample excitation chamber assembly 116 and an x-ray detector assembly 120. Assembly 110 also includes at least one x-ray focusing device (typically at least two devices) which is not shown. All these devices are integrated into a single assembly 110 having a housing 115.

Figure 8:
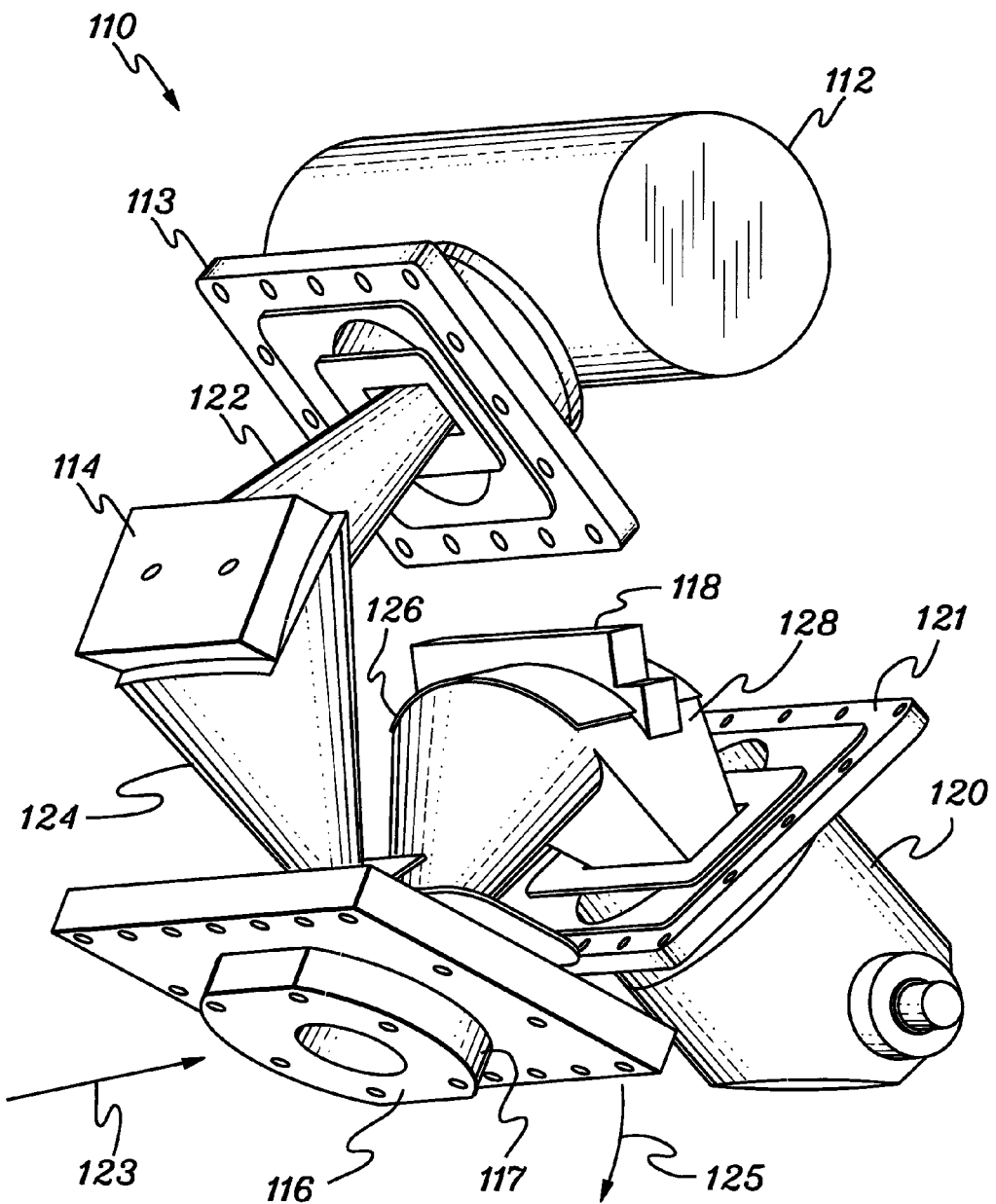
FIG. 8 is a perspective view of the aspect of the invention shown in FIG. 7 with the housing removed.

FIG. 8 illustrates the x-ray fluorescence system 110 shown in FIG. 7, but with housing 115 removed to show the representative spatial relationship between x-ray source assembly 112, sample excitation chamber assembly 116, x-ray detector assembly 120, and two x-ray focusing devices 114, 118. In a fashion analogous to the system 10 shown in FIG. 1, x-ray source assembly 112 produces an x-ray beam 122 which is focused by x-ray focusing device 114 to produce a focused beam 124 on a sample under test in excitation chamber assembly 116. The x-ray fluorescence created by the x-ray irradiation of the sample in sample excitation chamber assembly 116 generates x-ray flourescent beam 126. Beam 126 is focused by x-ray focusing device 118 to provide a focused x-ray beam 128 which is directed to x-ray detector assembly 120. Source assembly 112, holder assembly 116, and detector assembly each include mounting flanges 113, 117, and 121, respectively for mounting each assembly to housing 115. X-ray focusing devices 114 and 118 also include means for mounting these device to housing 115.

In prior art methods of XRF detection, for example, in the D2622 method, the sample excitation path and detection path are maintained in an inert gas atmosphere, for example, in a helium atmosphere. However, the availability of inert gases, especially in remote locations, makes the implementation of these prior art processes inconvenient. In contrast, in one aspect of the present invention, the sample excitation path and the detection path are maintained under vacuum and no inert gas is necessary. For example, in system 110 shown in FIGS. 7 and 8, housing 115 is held under vacuum, for example, at least about 15 torr. Vacuum can be provided by a venturi pump having no moving parts. However, if desired and available, an in another aspect of the invention, an inert gas such as nitrogen or helium can be introduced and maintained in housing 115, for example, under pressure. In another aspect of the invention, housing 115 may be heated or cooled, for example, heated or cooled by means of a direct or indirect heat exchanger or via radiant or convective heating or cooling means. In another aspect of this invention, housing 115 may be unpressurized and contain essentially atmospheric pressure and temperature.

X-ray source assembly 112 may include any type of x-ray source, but source assembly 12 preferably includes a source similar or identical to source assembly 82 shown in FIGS. 4, 5, and 6. That is, source assembly 112 preferably includes an x-ray tube assembly having a thermally-conductive dielectric, such as material 70, and is adjustably mounted to its housing and is registerable to adjacent components, for example, to housing 115 via dowel pins or dowel holes.

X-ray focusing devices 114 and 118 may be any one of the focusing devices discussed previously, for example, a doubly-curved crystal or a polycapillary optic. Though x-ray focusing devices 114 and 118 illustrated in FIG. 8 are shown as doubly-curved crystals, other types of x-ray optics may also be used for system 110, including polycapillary, monolithic x-ray optics as disclosed in the above-referenced U.S. patents.

In some prior art XRF methods (again, for example, the D2622 method) the excitation of the sample is practiced using polychromatic x-rays. Among other things, the use of polychromatic x-ray excitation requires the use of at least two x-ray wavelengths in order to correct for errors inherent in polychromatic excitation. According to one aspect of the present invention, excitation, for example, by means of x-ray focusing device 114, is practiced using monochromatic x-rays. The use of monochromatic excitation avoids the need to correct detection errors which is typically required when using polychromatic excitation. For example, in one aspect of the present invention, background radiation levels are reduced since there is no Bremsstrahlung illumination. As a result, the present invention provides a higher signal to noise ratio than prior art methods using polychromatic excitation.

X-ray sample excitation chamber assembly 116 may comprise any type of cavity or surface for holding or retaining a sample for testing, for example, a solid, liquid, or gas sample. In one aspect of the invention, sample excitation chamber assembly 116 includes conduits 123 and 125 for introducing and removing, respectively, a sample from the sample excitation chamber 116, for, example, for continuous fluid (that is, gas or liquid) analysis.

Prior art XRF methods (for example, the D2622 method) typically require sample sizes of at least 25 mm in diameter, often much larger. In one aspect of the present invention, having an x-ray focusing device, the sample diameter may be less than 25 mm in diameter, even less than 10 mm in diameter, or even less than 3 mm in diameter. The capability to have such small sample diameters allows for smaller illumination areas and more reliable excitation and detection.

X-ray detector assembly 120 may comprise any type of x-ray detector capable of receiving an x-ray beam 128, for example, a focused x-ray beam. Detector assembly 120 may include a proportional-counter type x-ray detector or a semiconductor type x-ray detector. In one aspect of the invention, x-ray detector 120 includes at least one PIN-diode-type x-ray detector.

Typical prior art XRF methods (again, for example, the D2622 method) use proportional counters for x-ray detectors. However, proportional counter-type detectors typically require large detection areas or long detection times to count as many photons as possible. Also, proportional counter-type detectors typically have "windows" over their detection areas. Though for high-energy x-rays the presence of the window is inconsequential, when low-energy x-rays are detected using a proportional counter-type detectors, the presence of the window can interfere with the transmitted x-rays. Making the window thinner to avoid such interferences, increases the potential for gas leakage. However, in one aspect of the present invention, having excitation x-rays focused on the detector avoids the need for large detection areas, long detection times, or windows which characterize proportional counter-type detectors.

Another type of detector used in prior art methods (such as the D2622 method) use semiconductor-type detectors. Semiconductor-type detectors are typically preferred over proportion-counter-type detectors because, among other things, semiconductor-type detectors are smaller in size. For example, proportion-counter-type detectors typically have detector areas about 500 times larger than the detector areas of semiconductor-type detectors. In addition, semiconductor-type detectors achieve higher resolutions and better distinguish x-ray energies than proportional-counter-type detectors. However, semiconductor-type detectors are typically limited in size because as the size of the semiconductor-type detector increases, the semiconductor "leakage current" increases producing undesirable detection noise. On the other hand, reducing the size of semiconductor-type detectors reduces detection noise due to leakage current. However, typically, semiconductor-type detectors are also limited in how small a detector can be since detector detection efficiency begins to decline as the semiconductor-type detector gets smaller.

Typically, to increase the performance of semiconductor-type detectors, the semiconductor type devices are cooled, for example, cooled anywhere from about minus 10 degrees C. to about 77 degrees Kelvin. However, cooling such devices is expensive and inconvenient. In addition, cooling semiconductor-type detectors introduces the potential to form condensation on the detector which interferes with detector performance. One method of reducing the potential for condensation to form on a cooled detector is to maintain the detector behind a window in a inert gas environment, for example, using nitrogen. Sometimes a vacuum is used instead of an insert gas to limit the heat transfer present due to the inert gas. However, again, the use of inert gases or vacuum for a semiconductor-type detector is inconvenient and expensive and preferably is avoided.

Some of the shortcomings of the use of semiconductor-type detector are avoided or overcome by the present invention. First, due to the focusing of the excitation beam using x-ray focusing devices, the large detection areas of the proportional-counter-type detectors are avoided. The focusing of x-rays according to the present invention is more amenable to semiconductor-type detectors. The focusing and concentration of x-ray energy or flux according to the present invention, especially the use of monochromatic x-rays, somewhat counteracts the loss in resolution that typically occurs as the size of semiconductor-type detectors decrease. As a result, according to one aspect of the present invention, a semiconductor type detector can be operated at temperatures greater than −10 degrees centigrade, for example, greater than 0 degrees centigrade, or greater than 10 degrees centigrade, or even at about room temperature (about 20 degrees centigrade) or above, with little appreciable loss in performance, for example, compared to the performance of a proportional counter-type detector.

In addition, without the need for cooling, which typically requires some form of protective "window" in order to avoid condensation on the cooled surface, according to one aspect of the present invention, no protective window is required. That is, one aspect of the present invention is a windowless semiconductor-type x-ray detector for use at a temperature above 0 degrees centigrade or at about room temperature or above.

One type of semiconductor-type detector that can be used in an x-ray fluorescence system is a PIN-diode type semiconductor detector, for example, a Silicon-PIN-diode. The specifications for one such PIN-diode detector according to one aspect of the present invention appear in Table 1. The PIN-diode according to the present invention may be mounted to a pre-amplifier board and attached to an amplifier by means of a cable.

TABLE I

PIN-diode-type X-ray Detector Specifications

| Type | Si-PIN |
|---|---|
| Active area (diode) | 2.4 mm × 2.4 mm (5.6 mm$^2$) |
| Thickness (diode) | 500 μm |
| Detector window | 8 μm DuraBeryllium |
| Detector housing | TO-8 header 0.600 inch diameter |
| Collimator Type | 0.060 inch Aluminum |
| Detector Pre-amplifier with Detector | 2 inch × 1 inch circuit board |
| Amplifier Board | 3 inch × 5 inch circuit board |
| Cable Length | 0 to 6 feet |
| Detector Resolution, Mn Kα ($^{55}$FE) | 500 eV (typical) at 25 degrees C. |
| Detector Resolution, Mn Kα ($^{55}$FE) | 700 eV (typical) at 40 degrees C. |
| Peek to Background | to be determined |
| Energy conversion (Max.) | 5 mV/KeV (Typical); 10 mV/KeV |
| Lowest Detection limits | 1 KeV |
| Peak Shift | 2% at a temp. betw. 25–40 degrees C. |
| Noise counts | <0.01 cps at a temp. of 25 degrees C. |
| Power Supply Input | +/− 12 V (Typical) |
| Low Level Discriminator | 0 V (Min.) 9 V (Max.) |
| High Level Discriminator | 0 V (Min.) 9 V (Max.) |
| Energy Out Pulse | 9 V (Max.) |
| TTL Out Pulse | 5 V (Typical) |

Figure 9:
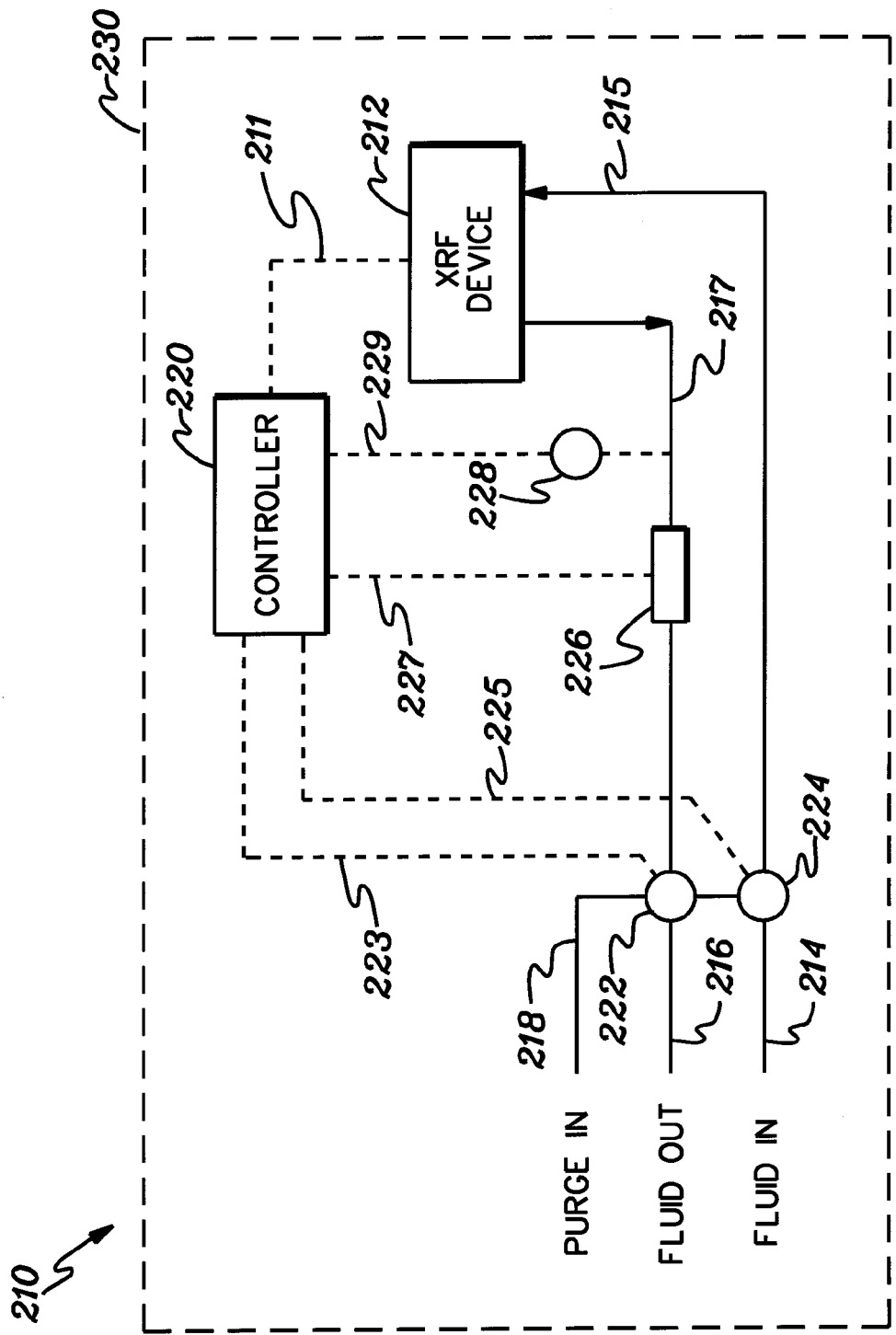
FIG. 9 is a schematic block diagram of an x-ray fluorescence system according to another aspect of the present invention.

FIG. 9 illustrates an x-ray fluorescence system 210 for analyzing fluids, typically continuously, according to another aspect of the present invention. X-ray fluorescence analyzing system 210 typically comprises at least one x-ray fluorescence assembly 212, for example, the x-ray fluorescence system 110 shown in FIGS. 7 and 8, having an x-ray source assembly 112, an x-ray sample excitation chamber assembly 116, an x-ray detector assembly 120 and one or more x-ray focusing devices 114, 118, though other assemblies performing similar functions may be used. System 210 also includes a fluid inlet 214, a fluid outlet 216, and a fluid purge inlet 218. Inlet 214, outlet 216 and purge inlet 218 may also include manually or automatic isolation valves (not shown). The fluid introduced to fluid inlet 214 may by any type of liquid or gas that can be analyzed via x-ray fluorescence, but in one aspect of the invention the fluid is a fuel, for example, a fluid fuel, such as a petroleum-based fuel, for example, gasoline, diesel fuel, propane, methane, butane, or coal gas, among others. One constituent of petroleum-based fuels that can be detected via x-ray fluorescence is sulfur, though other constituents can also be detected. In one aspect of the invention, the fluid analyzed by system 210 is diesel fuel in which the content of sulfur in the diesel fuel is characterized, for example, the concentration of the sulfur is determined. A system for characterizing the sulfur content in diesel fuel is marketed under the trademark SINDIE™ by X-Ray Optical Systems, Inc. of Albany, N.Y.

The flow of fluids through 210 is regulated and monitored by means of various conventional flow and pressure control devices, for example, one or more control valves 222, 224, flow meters, 226, and pressure indicators 228. Control valves 222, 224 are typically two- or three-way valves and may be manual or automated control valves. The control and operation of system 220 may be manually controlled or automatically controlled via controller 220. Controller 220 typically contains one or more conventional Programable Logic Controllers (PLC), power inputs, power conditioners, signal inputs, signal processors, data analyzers, input devices and output devices. Controller 220 receives input signals from and directs appropriate control systems to the monitoring and control devices via the various electrical connections shown in phantom in FIG. 9. System 210 can be housed in one or more cabinets, housings, or enclosures 230, for example, the fluid handling devices may be located in one cabinet and the controller 220 located in a separate cabinet. The cabinet or enclosure is typically a NEMA 4/12 purged enclosure. System 210 may be stationary or portable.

The following description will specifically describe the application of the present invention for the detection of sulfur in diesel fuel, that is, the SINDIE™ System, but it will be apparent to those of skill in the art that the present invention is applicable to other constituents of diesel fuel or to other fluids containing sulfur or other constituents. The operation of system 210 proceeds as follows. The x-ray analysis assembly 212 is energized, for example, via electrical connection 211 from controller 220. Diesel fuel, typically containing at least some sulfur, is introduced to system 210 via inlet 214 and passes through valve 224 and into x-ray analysis assembly 212 via conduit 215. The diesel fuel is introduced to the x-ray exposure chamber of x-ray exposure assembly in system 212 (for example, via conduit 123 in FIG. 8) where the diesel fuel is exposed to x-rays and at least some of the sulfur x-ray fluoresces and the presence of sulfur is detected by system 212. An electrical signal corresponding the sulfur detected by system 212 is transmitted to controller 220 for data analyses and or display. The diesel fuel exits the exposure chamber (for example, via conduit 125 in FIG. 8) and passes through conduit 217 and is discharged from system 210 via outlet 216. The pressure and rate of flow of fuel in conduit 217 may be detected, respectively, by flow measuring device 226 (for example, a rotometer) and pressure indicator 228 (for example, a pressure gauge) and corresponding signals forwarded to controller 220 via electrical connections 227 and 228, respectively. The direction of flow through (and the flow rate through) valves 222 and 224 may be regulated by controller 220 via control signals 223 and 225, respectively, for example, in response to the flow and pressure detected by flowmeter 226 or pressure indicator 228. Purge inlet 218 may be used to introduce a liquid or gas purge to the system, for example, water, air, or nitrogen, or to introduce fuels having known sulfur content for system calibration. The direction and flow of purge can be controlled either manually or automatically via valves 222 and 224.

Again, it will be apparent to those of skill in the art that the compact and robust design of system 210, that is, the SINDIE™ System, is amenable to the analysis of many types of fluids. However, when used for analyzing petroleum-based fuels, system 210 can be use for sulfur analysis at the crude oil well, at the oil storage facilities, in fuel refineries, anywhere in the fuel distribution pipeline or network, or anywhere else where the sulfur content of a petroleum-based fuel is desired. The use of system 210 eliminates the need for sample preparation and analytical reagents as is typically required in conventional methods of sulfur analysis of fuels. System 210 provides continuous, rapid, on-line fuel sulfur content so that a quality assessment and control can be effected as quickly as possible. Some of the analytical and physical specifications for the system shown in FIG. 9 appear in Table II.

TABLE II

Analytical and Physical Specifications for the Aspect of the Invention Shown in FIG. 9

| | |
|---|---|
| Detection Range | 5 ppm (mg/kg) to 50,000 ppm |
| Limit of Detection | 1 ppm (typical) |
| Repeatablity | 5% RSD (10–200 ppm) |
| Operating Temperature | minus 18 to 50 degrees C. |
| Communications | RS 232/485 serial output base 10T/Ethernet |
| Device Net | Profibus-DP and optional DCS system |
| Remote Diagnostic Capabilities | Yes |
| Maximum input fuel stream pressure | 100 PSIG |
| Nitrogen Gas Purge | Dry, at 80–100 PSIG |
| Power | 110 VAC 50/60 Hz, 500 Watts |
| Weight | 250 lbs. (approx.) |
| Dimensions | 78 inches H × 24 inches W × 18 inches D |

IMPROVED HEAT DISSIPATING ASPECTS OF THE INVENTION

Figure 10:
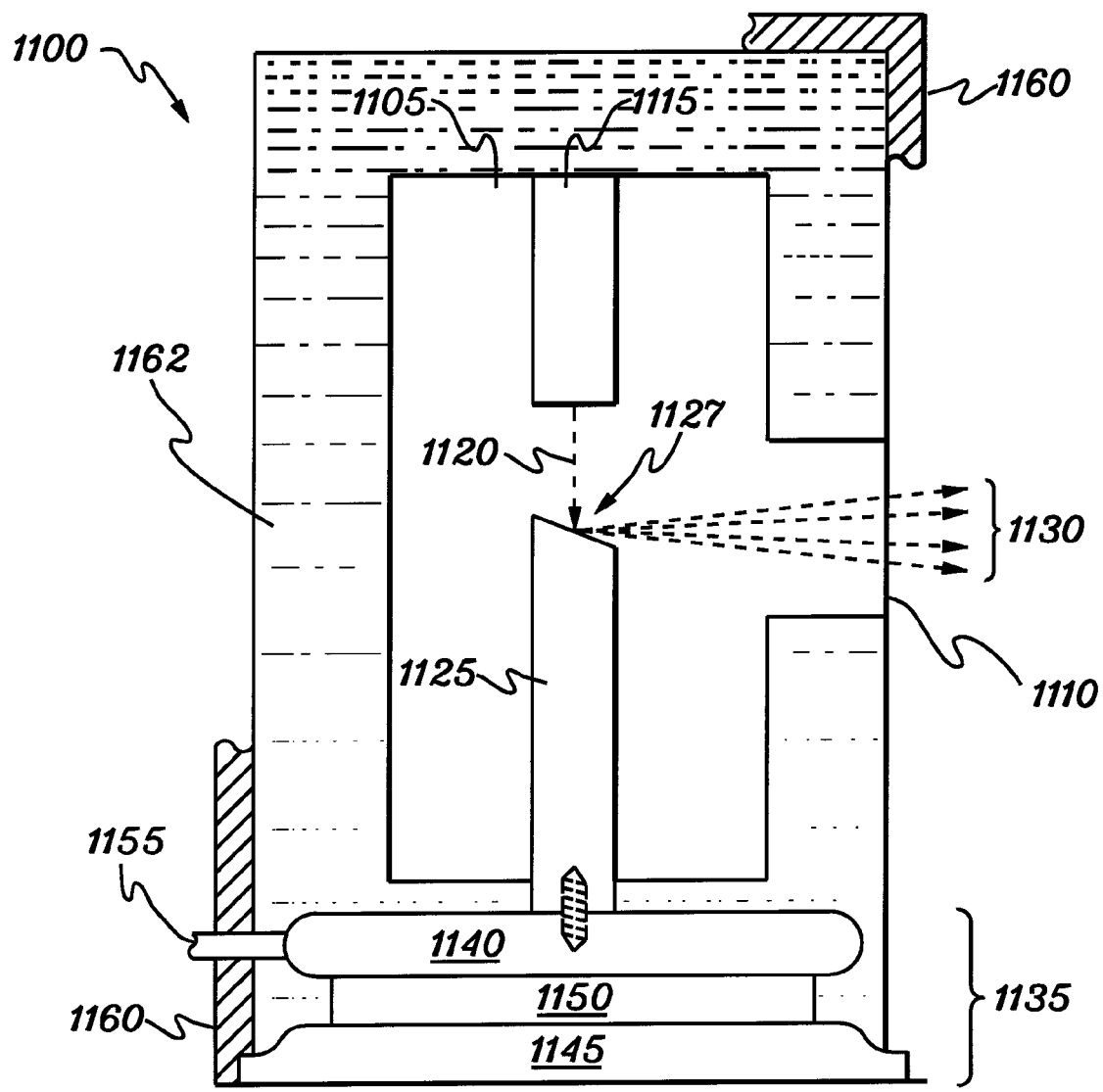
FIG. 10 illustrates a cross-sectional elevation view of one embodiment of a high-voltage component and a cooling and electrically-insulating device in accordance with one aspect of the present invention.

In accordance with a further heat dissipating aspect of the present invention, FIG. 10 illustrates a cross-sectional view of an x-ray beam assembly 1100 having a high-dielectric-strength and thermally-conductive cooling and electrically-insulating device, in accordance with one aspect of the invention. X-ray beam assembly 1100 includes an x-ray impermeable enclosure 1160 containing a vacuum-tight x-ray tube 1105 typically formed of glass or ceramic that has a transmission window 1110. In FIG. 10, enclosure 1160 is only shown partially, but it is to be understood that enclosure 1160 typically may surround the entire x-ray beam assembly 1100. X-ray tube 1105 houses an electron gun 1115 arranged opposite a high-voltage (HV) anode 1125. Electron gun 1115 is a device that, due to a voltage gradient, emits electrons in the form of an electron stream, that is, an electron beam (e-beam) 1120, as is well known in the art. HV anode 1125 acts as a target upon which an electron stream impinges and as a result produces x-ray radiation 1130, that is, x-rays, as is also well-known in the art.

Electron gun 1115 is typically held at ground potential (for example, about zero volts) and HV anode 1125 is held at a high voltage potential, typically, at about 50 kv or above. As a result, the e-beam 1120, which is emitting from electron gun 1115 at ground potential, is electrically attracted to the surface of HV anode 1125, which is at high voltage potential, thereby producing x-rays 1130. E-beam 1120 impinges anode 1125 and X-rays 1130 are emitted from anode 1125 from a location on anode 1125 referred to as the "focal spot" 1127 of the x-rays 1130. The angle of orientation of the surface of anode 1125 at focal spot 1127 allows x-rays 1130 to be directed toward transmission window 1110. Transmission window 1110 is typically formed of an x-ray transmissive material, such as beryllium (Be), or the like, which allows x-rays 1130 to exit x-ray beam assembly 1100, while maintaining the vacuum within x-ray tube 1105. In one aspect of the invention, for example, when higher energy x-rays are used, for instance, 20 Kev photons or higher, no window may be needed, the x-rays may pass through the x-ray tube, for example, a glass x-ray tube, without the need for a window.

The end of HV anode 1125 opposite the impingement surface typically protrudes through the body of x-ray tube 1105 and is mechanically, thermally, or electrically coupled (for example, connected) to a base assembly 1135. According to one aspect of the invention, base assembly 1135 is a three-plate structure that includes a first plate 1140 made from a thermally-conductive material, a second plate 1150 made from a dielectric material, and third plate, or base plate, 1145 made from a thermally-conductive material. First plate 1140 is at least partially electrically isolated from third plate 1145 by means of second, dielectric plate 1150. In one aspect of the invention, first plate 1140 functions as a thermal spreader, that is, plate 1140 receives heat from anode 1125 over a limited area, for example, a small centrally-located limited area on plate 1140, and distributes the heat to a larger area of plate 1140 to facilitate further dissipation of the heat. Base assembly 1135 may be mounted to housing 1160. In one aspect of the invention, base assembly 1135 supports at least anode 1125 and may support x-ray tube 1105. In one aspect of the invention, plate 1140 and anode 1125 comprise a single integral component, for example, a component machined from a single piece of metal or forged as a single component. In another aspect of the invention, plate 1140 and anode 1125 are separate components which are mated by conventional means, for example, by soldering, brazing, welding, or by means of an adhesive, for example, an electrically conductive adhesive. In one aspect of the invention, base assembly 1135 provides the only structural support for x-ray tube 1105. Further details of the interconnections within base assembly 1135 are provided in FIG. 11.

In one aspect of the invention, plate 1140, plate 1145, or both plates 1140 and 1145 may comprise a coating or layer of conductive material on plate 1150 (or on a similar structure, such as, a bar, block, or cylinder). In one aspect of the invention, the coating or layer of conductive material corresponding to plate 1140, plate 1145, or both plates 1140 and 1145 may comprise a layer of conductive material (for example, copper, etc.) disposed on or applied to plate 1150 (or a similar structure) by chemical vapor deposition or sputtering, among other methods.

According to another aspect of the invention, base assembly 1135 may comprise a single plate or component structure, for example, a single plate 1150 (or similar structure, such as, a bar, block, or cylinder) made of a thermally-conductive dielectric material, and plate 1140 and plate 1145, or corresponding structures, may be omitted. Plate 1150 may be disposed directly on anode 1125 and provide a sufficient thermal path for cooling anode 1125.

In another aspect of the invention, base assembly 1135 may comprise a two-plate or two-member structure in which plate 1140 or plate 1145 (or equivalent structures) may be omitted. In one aspect of the invention, anode 1125 may be disposed on a thermally-conductive dielectric material such as plate 1150 (or on a-similar structure, such as, a bar, block, or cylinder) and electrically-conductive plate 1145 may be disposed on plate 1150 (or on a similar structure) and provide a sufficient thermal path for cooling anode 1125. In one aspect of the invention, the function of electrically-conductive plate 1145 (or its equivalent) may be provided by a layer or coating of conductive material applied to a thermally-conductive dielectric material, such as plate 1150 (or a similar structure). In one aspect of the invention, the layer or coating of conductive material (for example, copper) may be applied by chemical vapor deposition, sputtering, or similar processes. In one aspect of the invention, the function of thermally-conductive, dielectric plate 1150 may be provided by a layer or coating of thermally-conductive dielectric material applied to conductive plate 1145 (or its equivalent). In one aspect of the invention, the layer or coating of thermally-conductive dielectric material may be a diamond-like carbon (DLC), for example, a DLC applied to plate 1145 (or its equivalent) by means of chemical vapor deposition. In one aspect of the invention, the layer or coating of thermally-conductive dielectric material acts as a thermal spreader to distribute heat from anode 1125 to conductor plate 1145.

In addition, in another two-component aspect of the invention, anode 1125 may be disposed on a thermally-conductive, electrically-conductive material, such as plate 1140 (or on similar structure, such as, a bar, block, or cylinder) and a thermally-conductive, dielectric material (such as plate 1150 or similar structure) may be disposed on plate 1140 (or on a similar structure) and provide a sufficient thermal path for cooling anode 1125. Again, in one aspect of the invention, the function of electrically-conductive plate 1140 (or its equivalent) may be provided by a layer or coating of conductive material applied to thermally-conductive dielectric material such as plate 1150 (or on a similar structure).

In the double- and triple-component embodiments of the invention, plates 1140 and 1145 may be circular plates, for example, 2-inch diameter disk-shaped plates, though any conventionally-shaped plates, for example, triangular, square, or rectangular, may be used according to the invention. Plates 1140 and 1145 may be formed from a thermally-conductive material, for example, a highly thermally-conductive material, such as a copper-containing material, for instance, copper; an aluminum-containing material; a silver-containing material; a gold-containing material; a diamond material, for instance diamond-like carbon; or a combination of two or more of these materials. In one aspect of the invention, plates 1140 and 1145 may also comprise an electrically-conductive material, for example, one of the materials mentioned above. Plates 1140 and 1145 may have a thickness in the range of about 0.1 inches to about 0.5 inches, for example, a thickness of about 0.25 inches. In one aspect of the invention, plates 1140 and 1145 are about the same size, for example, may have about the same diameter. However, in one aspect of the invention, plates 1140 and 1145 are sized differently, for example, as shown in FIG. 10 plate 1145 may be larger in than plate 1140, for instance, larger in diameter. Base plate 1145 may also include some constructional or mounting arrangement to support and accommodate the overall structure of x-ray beam assembly 1100. In one aspect of the invention, the thickness of plate 1140, and of plate 1145, may be small compared to the surface area of plate 1140. For example, in one aspect of the invention, the ratio of the surface area (in square inches) to the thickness of plate 1140, or plate 1145, (in inches) may typically be at least about 5 to 1. In one aspect of the invention, the ratio of the surface area of plate 1140, or plate 1145, to its thickness may be between about 10 to 1 and about 100 to 1. In one aspect of the invention, the diameter of plate 1140 is about 2 inches and the thickness of plate 1140 is about 0.25 inches, which corresponds to an area to thickness ratio of about 12.5 to 1.

In the single-, double-, and triple-component embodiments of the invention, dielectric plate 1150 may also be a circular plate, though any conventionally-shaped plate may be used, as described above with respect to plates 1140 and 1145. Plate 1150 may be smaller than plates 1140 and 1145, for example, when plates 1140, 1145, and 1150 are circular in shape, plate 1150 may be smaller in diameter than plates 1140 and 1145. In one aspect of the invention, plate 1150 may be disk-shaped and about 1.5 inches in diameter. Plate 1150 may be formed from a material that provides high thermal conductivity at high voltages, such as a beryllium oxide ceramic, an aluminum nitride ceramic, a diamond-like carbon, or their derivatives or equivalents. As a result, dielectric plate 1150 may have a high dielectric strength while also being a good thermal conductor. For example, in one aspect of the invention, dielectric plate 1150 comprises a material having a thermally conductivity of at least about 150 Watts per meter per degree K (W/m/K) and a dielectric strength of at least about $1.6 \times 10^7$ volts per meter (V/m). Dielectric plate 1150 may have a typical thickness in the range of between about 0.1 inches and about 0.5 inches, for example, a thickness of about 0.25 inches. In one aspect of the invention, the thickness of dielectric plate 1150 may be small compared to the surface area of dielectric plate 1150. For example, in one aspect of the invention, the ratio of the surface area (in square inches) to the thickness (in inches) of plate 1150 may typically be at least about 5 to 1. In one aspect of the invention, the ratio of the surface area of dielectric plate 1150 to its thickness may be between about 5 to 1 and about 100 to 1. In one aspect of the invention, the diameter of plate 1150 has a diameter of about 1.5 inches and a thickness of about 0.25 inches which corresponds to an area to thickness ratio of about 7.0 to 1.

Beryllium oxide ceramic has a typical thermal conductivity that is about ⅔ that of copper while aluminum nitride ceramic has a thermal conductivity that is about ½ that of copper. In one aspect of the invention, beryllium oxide ceramic is used for forming dielectric plate 1150. In another aspect of the invention, aluminum nitride ceramic is used for forming dielectric plate 1150. In some applications, aluminum nitride ceramic is preferred because beryllium oxide is a toxic substance and is therefore not as desirable for a manufacturing process or for environmental reasons. In contrast, aluminum nitride ceramic is a cost-effective, non-toxic alternative to beryllium oxide that is easy to work with.

In one aspect of the invention, the conductor plates 1140, 1145 and the dielectric plate 1150 are flat to minimize the amount of bonding material between the plates. For example, in one aspect of the invention, the surfaces of disks 1140 and 1145 and the surfaces of disk 1150 are flat to within at least about 0.001 inches.

In one aspect of the invention, HV anode 1125 is at least thermally connected to plate 1140. In another aspect of the invention, anode 1150 is at least thermally and electrically connected to plate 1140. In still another aspect of the invention, anode 1125 is mechanically, thermally, and electrically connected to plate 1140 of base assembly 1135. In another aspect of the invention, plate 1140 may be at least electrically connected to a high voltage source, for example, via a HV lead 1155. In another aspect of the invention, plate 1140 is mechanically, thermally, and electrically connected to a high voltage source, for example, via HV lead 1155. HV lead 1155 may be attached to plate 140 as disclosed in copending application Ser. No. 10/206,531 filed on Jul. 26, 2002, that is, filed on the same day as the present application, the disclosure of which is incorporated by reference herein. As a result, in one aspect of the invention, the high voltage potential is supplied to plate 1140 and also to HV anode 1125. Conversely, base plate 1145 is typically held at about ground potential. In one aspect of the invention, dielectric plate 1150 provides electrical isolation between the high-voltage plate 1140 and the grounded base plate 1145. Again, further details of all interconnections are provided below with reference to FIG. 11.

In another aspect of the invention, high-voltage cable 1155 may electrically communicate with anode 1125 by means other than via plate 1140. For example, in one aspect of the invention, cable 1155 is directly connected to anode 1125, for example, by means of the electrical connection disclosed in copending application Ser. No. 10/206,531. For example, in one aspect of the invention, in which anode 1125 is disposed directly on a thermally-conductive dielectric material, such as plate 1150, cable 1155 may be connected directly to anode 1125. In another aspect of the invention, cable 1155 communicates with anode 1125 via other means, for example, means not related to structure 1135.

In one aspect of the invention, the x-ray tube 1105 with electron gun 1115 and HV anode 1125, base assembly 1135, and HV lead 1155, are housed in an enclosure 1160, thereby forming x-ray beam assembly 1100. Enclosure 1160 may be filled with an encapsulating material, also known as an encapsulant, 1162, for example, a potting material, such as a silicone potting material or its equivalent, which encapsulates the elements of x-ray beam assembly 1100. As shown in FIG. 10, some elements of the x-ray beam assembly 1100 may protrude beyond enclosure 1160, such as base assembly 1135. Enclosure 1160 encapsulant 1162 may form a structure that may be void of air pockets and may serve to isolate many surfaces of x-ray beam assembly 1100 from the ambient environment, for example, ambient air, via encapsulant 1162 or housing 1160. In one aspect of the invention, encapsulant 1162 comprises a material having a breakdown voltage of least about $1.6 \times 10^7$ V/m, for example, a silicone potting material or its equivalent. In another aspect of the invention, the thermal properties of encapsulant 1162 may not be critical to the function of encapsulant 1162, for example, the material comprising encapsulant 1162 may not need be a good conductor of heat. One material that may be used for encapsulant 1162 is a silicone material, for example, a silicone elastomer, such as Dow Sylgard® 184 silicone elastomer, or its equivalent.

Figure 11:
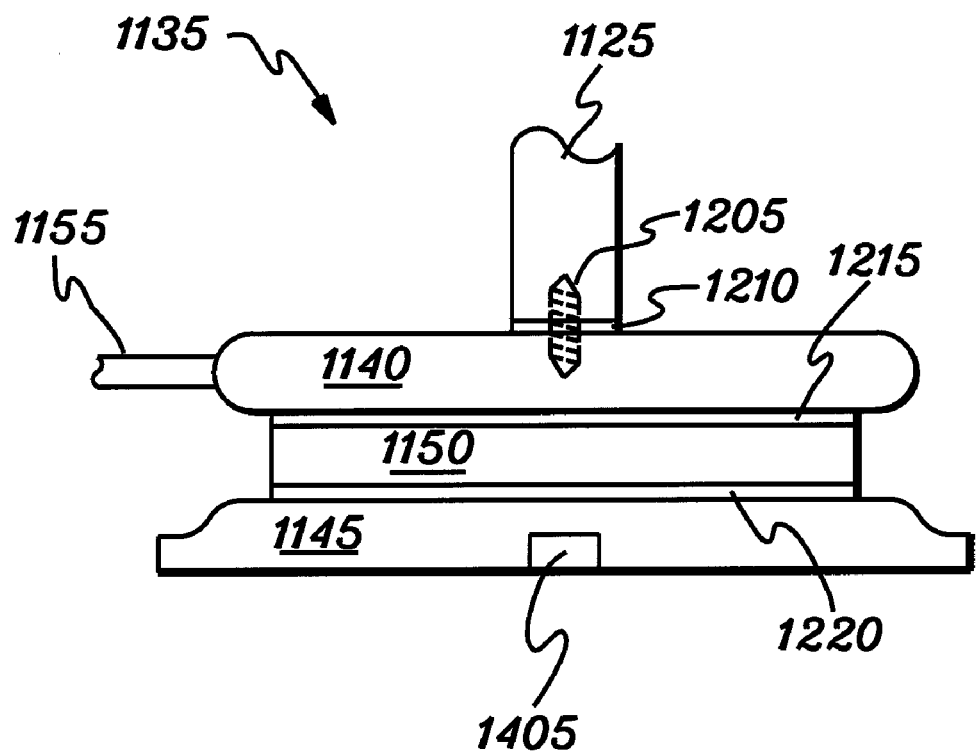
FIG. 11 illustrates a detail of the cooling and electrically-insulating device of FIG. 10 in accordance with one aspect of the present invention.

FIG. 11 illustrates a detailed cross-sectional view of base assembly 1135 according to one aspect of the present invention. In one aspect of the invention, base assembly 1135 serves as a high-dielectric-strength and thermally-conductive heat dissipating device. In another aspect of the invention, base assembly 1135 serves as a high-dielectric-strength and thermally-conductive heat dissipating device and a structural support for x-ray beam assembly 1100.

FIG. 11 illustrates that HV anode 1125 is at least thermally connected to plate 1140, though in one aspect of the invention, anode 1125 is mechanically, thermally, and electrically connected to plate 1140. In one aspect of the invention, anode 1125 is mechanically connected to plate 1140 via conventional means, for example, one or more mechanical fasteners, welding, brazing, soldering, adhesives, and the like. In one aspect of the invention, anode 1125 is connected to plate 1140 via a mounting stud 1205, a bonding layer 1210, or a combination thereof. Mounting stud 1205 may be a threaded stud formed from a conductive material, for example, steel, aluminum, copper, or one of the other conductive materials mentioned above. In the aspect of the invention shown in FIG. 11, mounting stud 1205 threads into both the HV anode 1125 and plate 1140. Bonding layer 1210 may be formed from, for example, a high-conductivity solder, such as, an indium-tin (In—Sn) solder, for instance, an In—Sn Eutectic solder, or its equivalent.

Plates 1140, 1145, and 1150 may also be connected to each other by conventional means, for example, using one or more mechanical fasteners, welding, brazing, soldering, adhesives, and the like. In one aspect of the invention, dielectric plate 1150 is connected to plate 1140 and plate 1145 is connected to dielectric plate 1150 via bonding layers 1215, 1220, respectively. Bonding layers 1215, 1220 may, for example, be a high-conductivity solder similar to the solder used for bonding layer 1210 described above. In one aspect of the invention, plate 1145 includes a means for supporting or mounting base assembly 1135, which may also support x-ray beam assembly 1100, or at least anode 1125. Though the means for supporting base assembly 1135 may be any conventional support means, in one aspect of the invention, plate 1145 includes at least one mounting hole 1405, for example, at least one threaded mounting hole.

X-ray beam assembly 1100 may include further means for conducting and dissipating heat from plate 1145. In one aspect of the invention, plate 1145 may be operatively connected to conventional means for conducting and dissipating heat from plate 1145. For example, plate 1145 may be operatively connected to one or more cooling fins or cooling pins. In another aspect of the invention, plate 1145 or the cooling fins or cooling pins may also be exposed to forced air cooling, for example, by means of a fan, for instance an electric fan mounted to x-ray beam assembly 1100.

According to one aspect of the invention, plates 1140 and 1145 comprise smooth edges, for example, radiused edges as shown in FIG. 11. According to this aspect of the invention, the radiused edges minimize the electric field gradients about the edges of the plates so as to reduce the potential for electric discharge between plates 1140 and 1145.

According to one aspect of the invention, base assembly 1135 provides mechanical support for x-ray beam assembly 1100, in particular support for high-voltage anode 1125, for example, with little or no direct support from the low voltage or grounded components of x-ray beam assembly 1100. According to one aspect of the invention, the mechanical support provided by base assembly 1135 also includes a thermal conduction path for removing heat from x-ray beam assembly 1100. In another aspect of the invention, in addition to mechanical support and thermal conduction, base assembly 1135 may also provide at least some electrical isolation, wherein little or no current is lost over base assembly 1135, that is, current loss from anode 1125, or from any other high-voltage components of x-ray beam assembly 1100, is minimized.

According to another aspect of the present invention, base assembly 1135 provides an effective mean of dissipating, for example, conducting, heat from x-ray beam assembly 1100, for example, from anode 1125. According to this aspect of the invention (see FIG. 10), heat generated by the impingement of beam 1120 on anode 1125 and the generation of x-rays 1130 is conducted from point of impingement 1127 along anode 1125 and into plate 1140. Plate 1140 then conducts heat from the point of contact of anode 1125, for example, in a radial direction, and distributes the heat to plate 1140, for example, uniformly distributes heat to plate 1140. The heat in plate 1140 is then conducted into plate 1150 and from plate 1150 the heat is conducted in plate 1145. According to one aspect of the invention, the distribution of heat in plate 1140 effectively distributes the heat in plate 1140 wherein the temperature difference across dielectric plate 1150 is minimized. As a result, the thermal conductivity of dielectric plate 1150 may be less than the conductively of conventional conducting materials, for example copper-containing materials, and still provide sufficient conductivity to dissipate heat from plate 1140 to plate 1145. The heat in plate 1145 may be further dissipated through conduction to mating structures or through natural convection, forced air convection, or flowing a cooling fluid over plate 1145. In one aspect of the invention, cooling pins or fins (not shown) may be attached to be operatively connected to plate 1145. In addition, according to one aspect of the invention, one or more dielectric plates 1150 and conducting plates 1145 may be mounted to plate 1140, for example, 2 or more sets of plates 1150 and 1145 may be used to conduct heat away from x-ray beam assembly 1100.

According to one aspect of the invention, an x-ray producing device is provided which requires little or no cooling fluids, for example, little or no internal cooling fluids. That is, one aspect of the invention, obviates the need to provide sealing means, leakage prevention, or replacement fluids that characterizes some prior art. In addition, according to another aspect of the invention, an x-ray producing device is provided which can more readily be adapted for adjustment or alignment of the x-ray beam. For example, without the presence or need for cooling fluids, an x-ray alignment or adjustment mechanism may be incorporated into x-ray device 1100, for example, for aligning x-ray beam 1130 with an x-ray optic, such as a capillary optic or crystal optic, without requiring the alignment or adjustment mechanism to be fluid tight. For example, one alignment mechanism that may be used with one aspect of the present invention is disclosed in copending application Ser. No. 60/336,584 filed Dec. 4, 2001, the disclosure of which has been incorporated by reference herein.

IMPROVED ALIGNMENT AND STABILITY ASPECTS OF THE INVENTION

As generally discussed above, the present invention provides in one aspect an x-ray source assembly providing, for example, a focused x-ray beam or a collimated x-ray beam, and having a stable output over a range of operating conditions. This stable output is obtained via a control system which controls positioning, in one aspect, of the anode source spot relative to an output structure of the assembly notwithstanding a change in one or more of the operating conditions. For example, the position of the anode source spot can be maintained constant relative to an output structure notwithstanding change in the anode power level or a change in the ambient temperature about the x-ray source assembly.

The control system employs one or more actuators which can effect movement of either the anode source spot or the output structure. For example, one actuator might comprise a temperature actuator which provides heating/cooling of the anode to effect adjustments in the anode source spot location relative to the output structure. Another actuator might comprise a mechanical actuator which would physically adjust position of either the anode source spot or the output structure as needed. Still another actuator might electrostatically or magnetically move the electron beam. One or more sensors can be employed by the control system to provide feedback on the anode source spot location relative to the output structure. The sensors may include temperature sensors, such as a sensor to directly or indirectly measure the anode temperature, as well as a housing temperature sensor and an ambient temperature sensor. The sensors may also include a feedback mechanism for obtaining the anode power level, or a direct or indirect measure of the optic output intensity.

In another aspect, an x-ray source assembly is disclosed which includes an x-ray tube having an anode for generating x-rays and an optic for collecting x-rays generated by the anode. A control system is provided for controlling x-ray output intensity from the optic. This control system can maintain x-ray output intensity notwithstanding a change in one or more operating conditions of the x-ray source assembly. For example, the control system can adjust for a change in anode power level and/or a change in ambient temperature. Various additional features of the invention are also described and claimed hereinbelow.

As used herein, the phrase "output structure" refers to a structure comprising part of the x-ray source assembly or associated with the x-ray source assembly. By way of example, the structure could comprise an x-ray transmission window or an optic, such as a focusing or collimating optic, which may or may not be secured to a housing surrounding the x-ray tube within the assembly.

Figure 12:
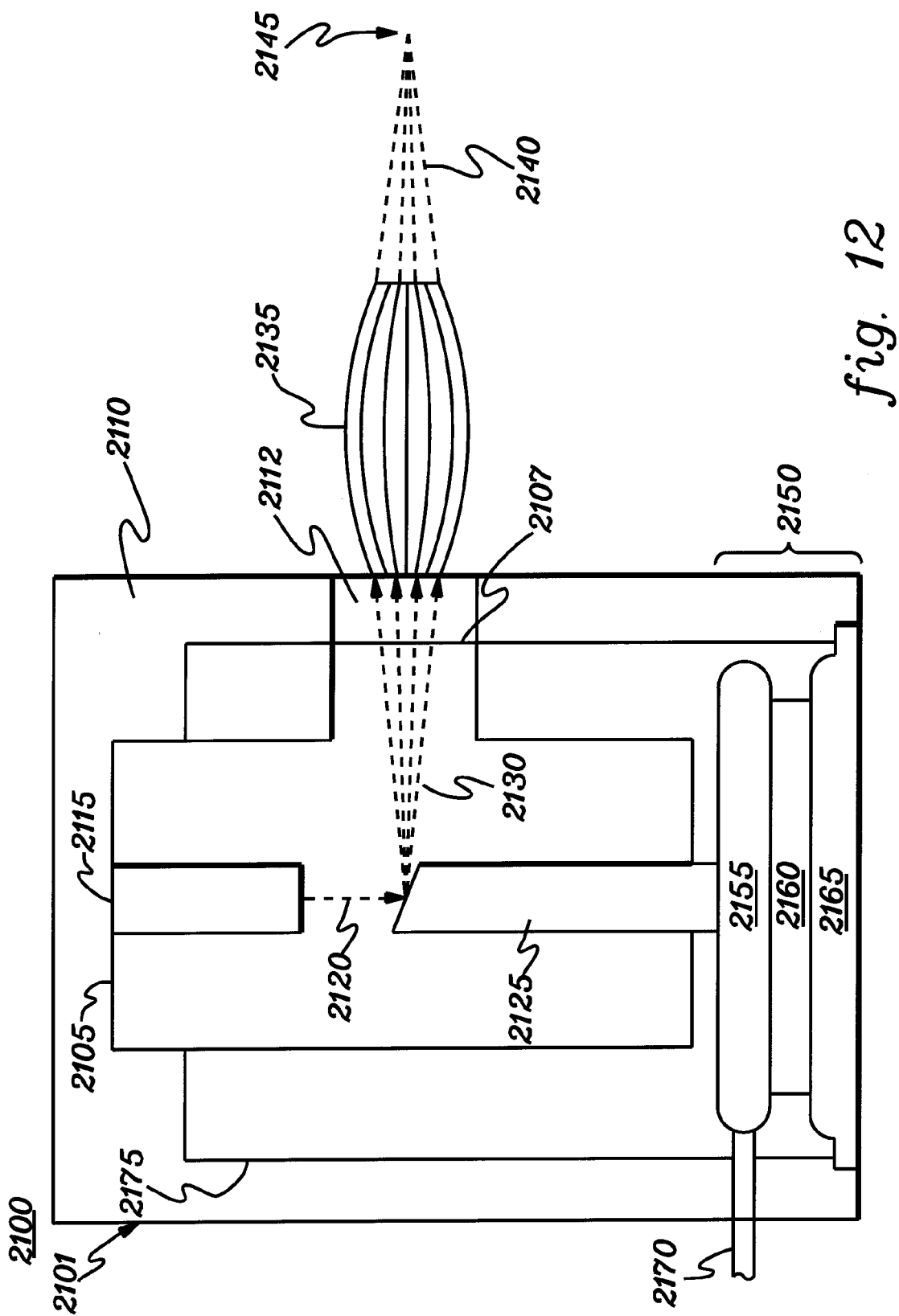
FIG. 12 depicts a cross-sectional view of one embodiment of an x-ray source assembly, in accordance with an aspect of the present invention.

FIG. 12 illustrates in cross-section an elevational view of an x-ray source assembly 2100 in accordance with an aspect of the present invention. X-ray source assembly 2100 includes a x-ray source 2101 comprising a vacuum tight x-ray tube 2105 (typically formed of glass or ceramic) having a transmission window 2107. X-ray tube 2105 houses an electron gun 2115 arranged opposite a high-voltage (LV) anode 2125. When voltage is applied, electron gun 2115 emits electrons in the form of an electron stream, i.e., an electron beam (e-beam) 2120, as is well known in the art. HV anode 2125 acts as a target with a source spot upon which the electron stream impinges for producing x-ray radiation, i.e., x-rays 2130.

By way of example, electron gun 2115 could be held at ground potential (zero volts), while HV anode 2125 is held at a high voltage potential, typically around 50 kv. As a result, e-beam 2120 emitted from electron gun 2115 at ground potential is electrically attracted to the surface of HV anode 2125, thereby producing x-rays 2130 from a source spot on the anode where e-beam 2120 strikes the anode. X-rays 2130 are subsequently directed through transmission window 2107 of vacuum tight x-ray tube 2105. Transmission window 2107 is typically formed of a material such as beryllium (Be) which permits substantially unimpeded transmission of x-rays while still maintaining the vacuum within x-ray tube 2105.

A housing 2110 at least partially encloses x-ray tube 2105. Housing 2110 can include an aperture 2112 aligned with transmission window 2107 of x-ray tube 2105. By way of example, aperture 2112 could comprise an open aperture in housing 2110 or an enclosed aperture defining an air space. Upon transmission through transmission window 2107 and aperture 2112, x-rays 2130 are collected by an optic 2135. Optic 2135 is shown in this example centered about aperture 2112 in housing 2110. Optic 2135 could be affixed to an exterior surface of housing 2110, or could be partially disposed within housing 2110 to reside within aperture 2112 (e.g., to reside against transmission window 2107), or could be separately supported from housing 2110 but aligned to aperture 2112 in housing 2110.

As noted, optic 2135 could comprise a focusing optic or a collimating optic, by way of example. In FIG. 12, optic 2135 is shown to be a focusing element, which is useful when x-ray source 2100 is utilized for applications requiring a high intensity, low diameter spot 2145. Focusing optic 2135 collects x-ray radiation 2130 and focuses the radiation into converging x-rays 2140. A focusing optic could be beneficial when x-ray source 2100 is to be employed in connection with an x-ray fluorescence system which requires a low power source. As an alternative, optic 2135 could comprise a collimating optical element for use in applications which require a parallel beam of x-ray radiation output from the optic (not shown). In the case of a collimating optical element, x-rays 2140 would be parallel rather than converging to spot 2145 as shown in FIG. 12.

Optic 2135 could comprise any optical element capable of collecting or manipulating x-rays, for example, for focusing or collimating. By way of example, optic 2135 could comprise a polycapillary bundle (such as available from X-ray Optical Systems, Inc. of Albany, N.Y.), a doubly curved optic or other optical element form, such as a filter, a pinhole or a slit. (A polycapillary optic is a bundle of thin, hollow tubes that transmit photons via total reflection. Such an optic is described, for example, in U.S. Pat. Nos. 5,175,755, 5,192,869, and 5,497,008. Doubly curved optics are described, for example, in U.S. Pat. Nos. 6,285,506 and 6,317,483) Upon calibration of x-ray source assembly 2100, optic 2135 remains stationary (in one embodiment) relative to x-ray source 2101 until further calibration of x-ray source assembly 2100 is performed.

The end of HV anode 2125 opposite the impingement surface protrudes through the body of x-ray tube 2105 and is mechanically and electrically connected to a base assembly 2150. Base assembly 2150 includes a first conductor disc 2155 that is electrically isolated from a base plate 2165 via a dielectric disc 2160. The resulting anode 2125 and base assembly 2150 structure, referred to herein as the anode stack, is described in detail in the above-incorporated, co-filed patent application entitled "Method and Device For Cooling and Electrically Insulating A High-Voltage, Heat Generating Component". Although described in greater detail therein, the structure and function of base assembly 2150 are briefly discussed below.

Conductor disc 2155 and base plate 2165 are, for example, several-inch diameter, disc-shaped plates formed of a highly electrically conductive and highly thermally conductive material, such as copper. By way of example, conductor disc 2155 and base plate 2165 may have a thickness in the range of 0.1 to 0.5 inches, with 0.25 inches being one specific example. Base plate 2165 may further include constructional detail to accommodate the overall structure of x-ray source 2101.

Dielectric disc 2160 is, for example, a 1.5-inch diameter, disc-shaped plate formed of a material that provides high dielectric strength at high voltages, such as beryllium oxide ceramic or aluminum nitride ceramic. In addition, while not as thermally conductive as conductor disc 2155 or base plate 2165, these materials do exhibit relatively good thermal conductivity. Dielectric disc 2150 may have a thickness in the range of 0.1 to 0.5 inches, with 0.25 inches being one specific example.

Conductor disc 2155 is mechanically and electrically connected to a high voltage source (not shown) via an appropriate high voltage lead 2170. As a result, the high voltage potential is supplied to conductor disc 2155 and subsequently to HV anode 2125. Conversely, base plate 2165 is held at ground potential. Dielectric disc 2160 provides electrical isolation between high-voltage conductor disc 2155 and the grounded base plate 2165. One example of an assembly for connecting high voltage lead 2170 to conductor disc 2155 is described in the above-incorporated, commonly filed patent application entitled "An Electrical Connector, A Cable Sleeve, and A Method For Fabricating A High Voltage Electrical Connection For A High Voltage Device".

The x-ray tube 2105, base assembly 2150, and HV lead 2170, are encased in an encapsulant 2175. Encapsulant 2175 can comprise a rigid or semi-rigid material with a sufficiently high dielectric strength to avoid voltage breakdown, such as silicone. Furthermore, encapsulant 2175 need not be a good thermal conductor since the preferred thermal path is through base assembly 2150. As a specific example, encapsulant 2175 could be formed by molding a silicon elastomer (such as Dow Sylgard® 184 available from Dow Chemical), around the x-ray tube, base assembly and high voltage lead, thereby forming a structure which is void of air pockets which might provide an undesirable voltage breakdown path to ground.

Figure 13:
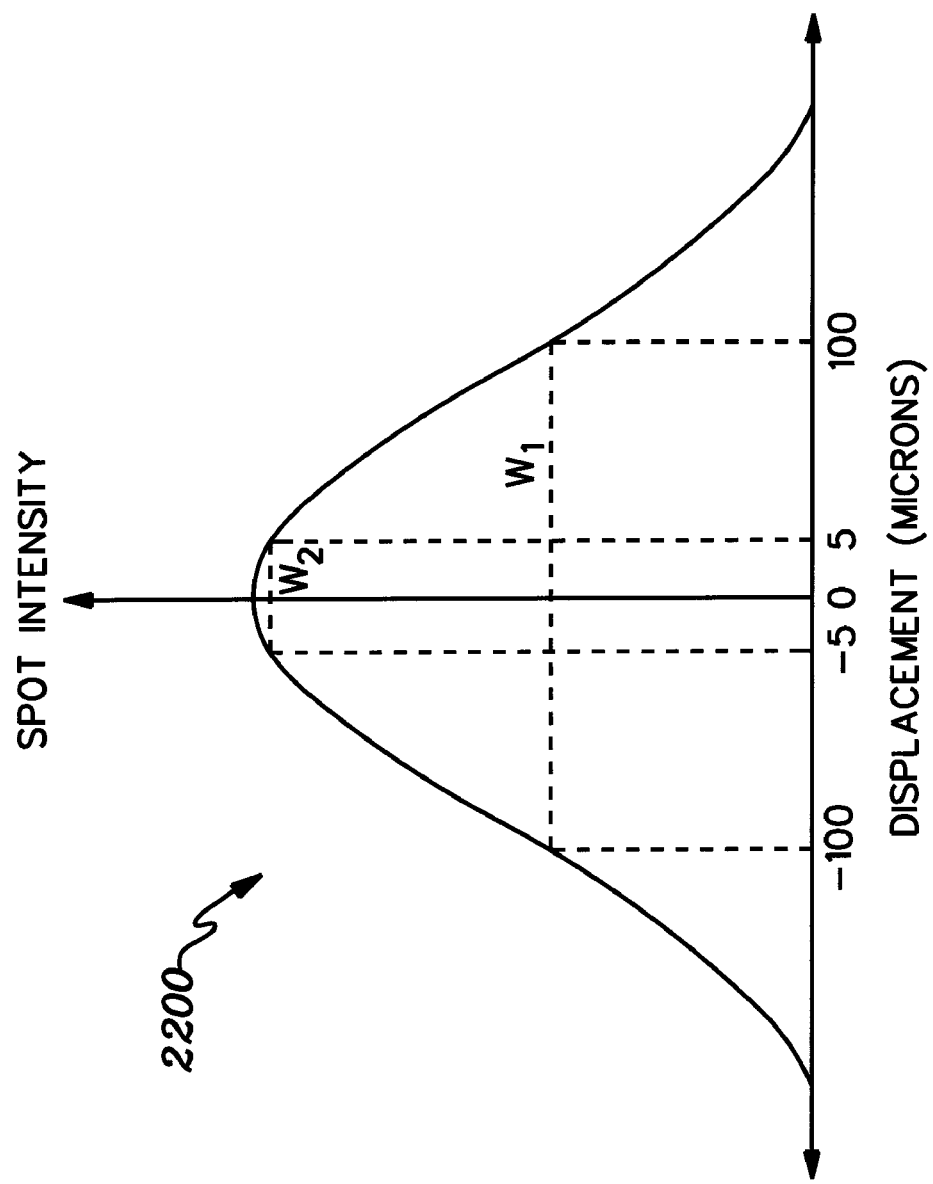
FIG. 13 depicts one example of a source scan curve for an x-ray source such as shown in FIG. 12 plotting output intensity versus displacement, in accordance with an aspect of the present invention.

FIG. 13 graphically illustrates a source scan curve 2200 in which a representation of output intensity, e.g., spot 2145 (FIG. 12) intensity, is plotted with respect to displacement or misalignment between the anode source spot and the output optic. The spot intensity results from scanning x-rays (2130) across the focal point of optic (2135). It is shown that a Gaussian plot results, in which a maximum intensity is achieved with proper alignment of x-rays 2130 (and thus the anode source spot) at the focal point of the optic.

As shown, the full width W1 at half maximum (FWHM) is equal to approximately 200 microns. A FWHM of 200 microns indicates that the x-ray intensity at spot 2145 drops 50% as a result of displacement of x-rays 2130 (and thus the anode source spot) a distance of 2100 microns from the focal point of optic 2135. When properly calibrated, x-ray source assembly 2100 functions for a given power near the top of the source scan curve of FIG. 13, where the slope is approximately equal to zero, such that minor perturbations in the displacement of x-rays 2130 (e.g., 5 μm or less) with respect to optic 2135 result in a negligible intensity drop. By way of example, the range of allowable perturbations in the displacement of x-rays 2130 with respect to optic 2135 is represented by W2, indicating that a displacement less than five microns between x-rays 2130 and the focal point of optics 2135 is acceptable. However, a difference in the thermal expansion of as much as 50 microns can occur in HV anode 2125 and the elements of base assembly 2150 as the operating power of the x-ray source varies from 0 to 50 W.

Figure 14:
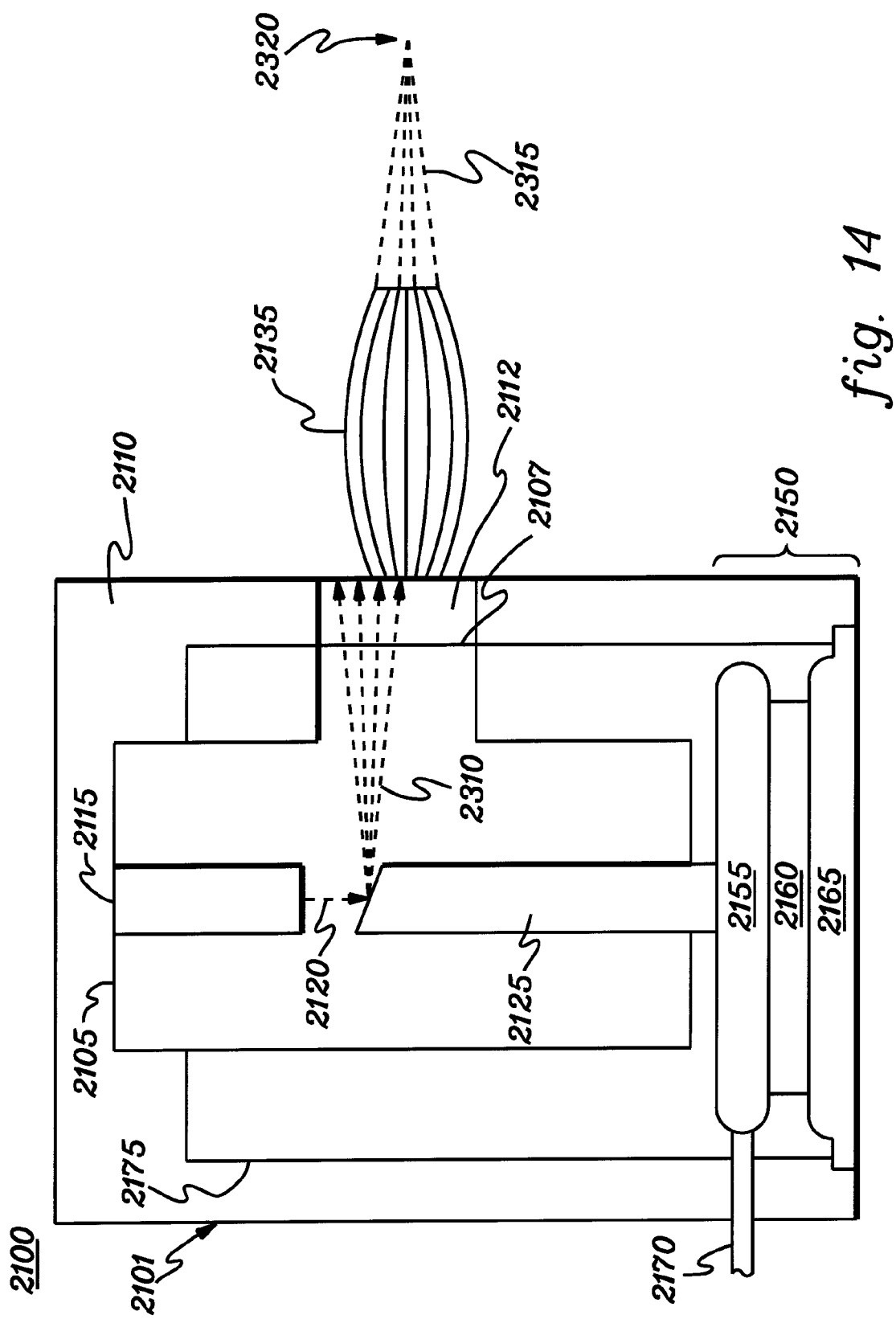
FIG. 14 depicts a cross-sectional view of the x-ray source assembly of FIG. 1 showing a source spot to optic misalignment, which is addressed in accordance with an aspect of the present invention.

FIG. 14 depicts x-ray source 2100 as described above in connection with FIG. 12. In this example, however, heat generated by e-beam 2120 impinging on HV anode 2125 has caused HV anode 2125, conductor disc 2155, base plate 2165, and to a lesser extent, dielectric disc 2160, to expand. As a result of this expansion, a divergent beam of x-rays 2310 is generated that is displaced vertically with respect to x-rays 2130 illustrated in FIG. 12. For example, if the electron gun 2115 is operated at a power of 50 W, the focal point of x-rays 2310 may be displaced by as much as 50 microns from its position at 0 W. X-rays 2310 are misaligned with optic 2135 and, as a result, the convergent beam of x-rays 2315 produces a spot 2320 of markedly reduced intensity.

Due to the physical nature of collimating optics and focusing optics, such as doubly curved crystals and polycapillary bundles, precise positioning of optic 2135 relative to the anode source spot is desirable for optimum collimation or focusing of x-rays 2315. As a result, a displacement of x-rays 2310 with respect to optic 2135 such as may result from thermal expansion of HV anode 2125 and base assembly 2150 can result in a spot 2320 having significantly reduced intensity, as illustrated graphically in FIG. 13.

Figure 16:
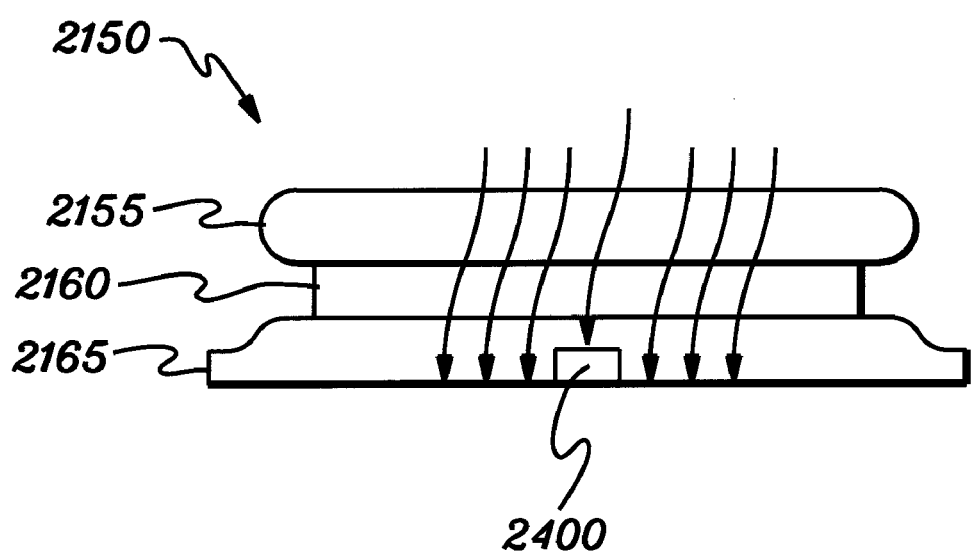
FIG. 16 is a cross-sectional view of one embodiment of the anode base assembly depicted in FIGS. 12, 14 & 15, in accordance with an aspect of the present invention.

The anode source spot to an output structure offset can be measured using various approaches. For example, a temperature sensor 2400 could be employed at the base of the anode stack to measure changes in anode stack temperature, which as described further below can be correlated to the anode source spot to optic offset during a calibration procedure. FIG. 16 shows an alternative temperature sensor implementation.

As shown in FIG. 16, base assembly 2150, again including conductor disc 2155, dielectric disc 2160 and base plate 2165, is modified to include a temperature sensor 2400 recessed within and in good thermal contact with base plate 2165. For illustrative purposes, FIG. 16 depicts waves which represent heat transfer from the anode, to and through the base assembly. These waves represent heat which is generated by the impingement of e-beam 2120 upon HV anode 2125 as shown in FIG. 15.

Figure 15:
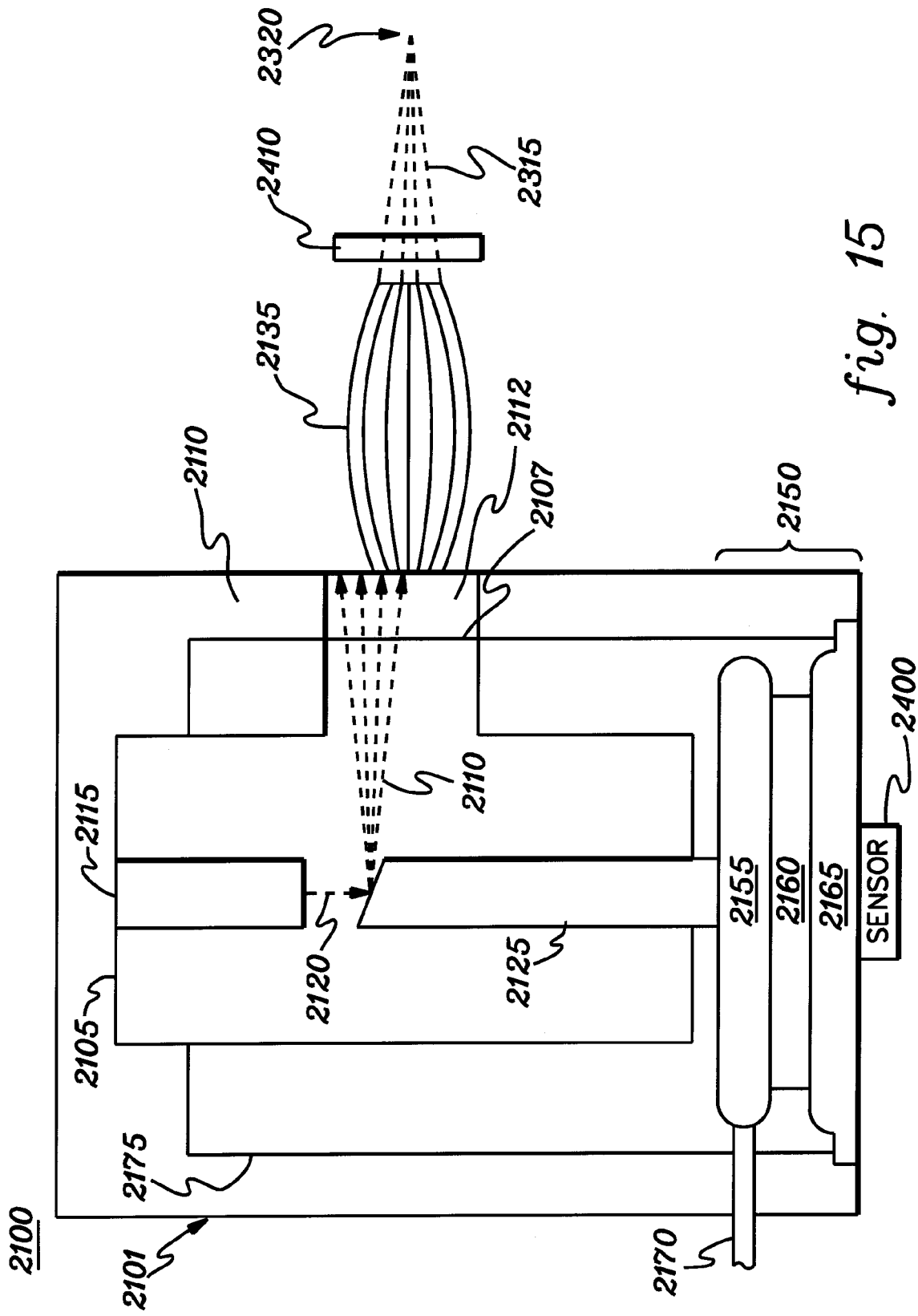
FIG. 15 depicts a cross-sectional view of the x-ray source assembly of FIG. 14 showing different sensor placements for monitoring source spot to optic displacement, in accordance with an aspect of the present invention.

Also depicted in FIG. 15 is an x-ray intensity measurement device 2410. In addition to, or as an alternative to, sensing temperature to determine offset, x-ray output intensity of either x-ray source 2101 or optic 2135 could be measured. By way of example, in a diffraction application, an ion chamber or a proportional counter could be used as an intensity measurement device 2410 in order to provide the needed feedback for a position control system such as described herein. In a diffraction application, the energy of interest is typically only at one wavelength and thus a proportional counter disposed within the x-ray path only absorbs a small amount of the x-rays of interest. Those skilled in the art will recognize that other intensity measurement approaches could be employed to directly or indirectly determine the intensity of x-rays output from the x-ray source assembly 2100. The goal of temperature sensing, x-ray intensity sensing, etc., is to provide feedback information on the alignment between the anode source spot and the output structure. A control system and a control process are described further below with reference to FIGS. 18–21.

Figure 17:
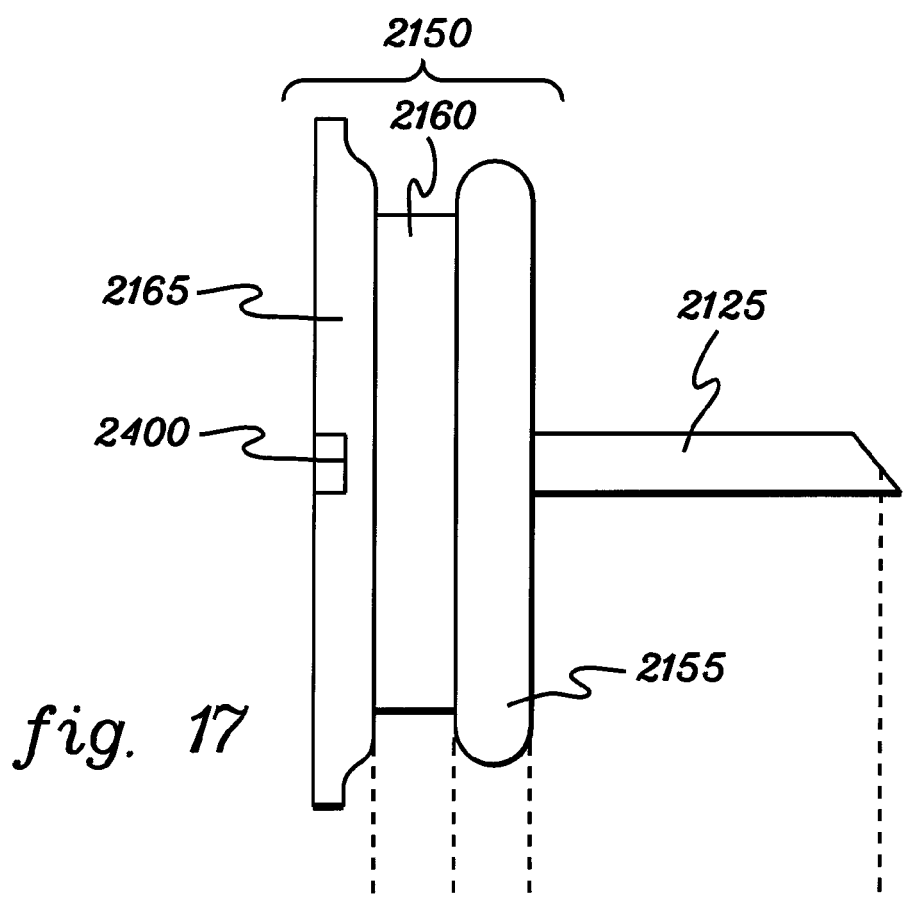
FIG. 17 is a cross-sectional view of the anode stack of FIGS. 12, 14 & 15, in accordance with an aspect of the present invention.
Figure 17A:
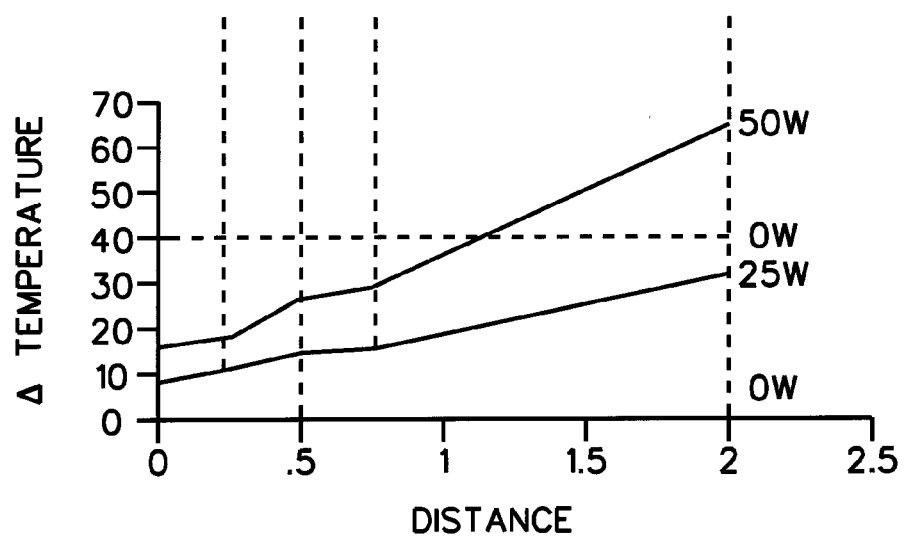
FIG. 17A is a graphical representation of change in temperature across the elements of the anode stack for different anode power levels, in accordance with an aspect of the present invention.
Figure 17B:
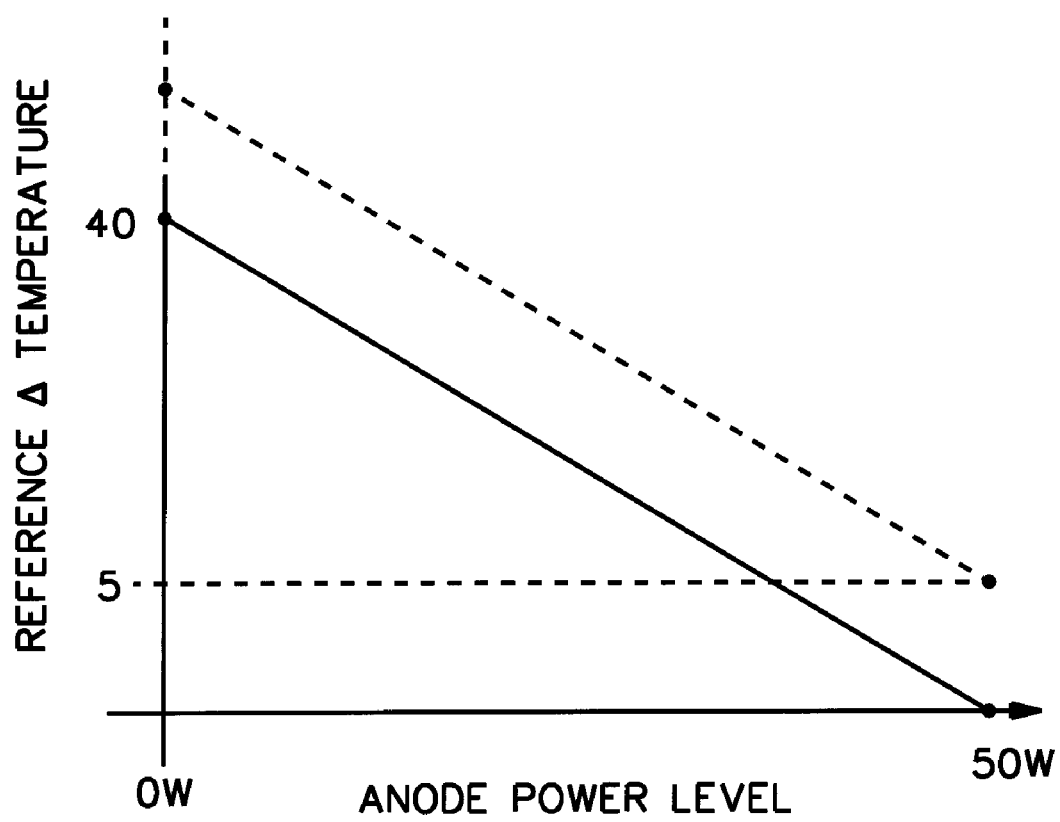
FIG. 17B is a graph of change in reference temperature as a function of anode power level, in accordance with an aspect of the present invention.

The correlation between anode stack temperature and anode source spot to output structure alignment can be better understood with reference to FIGS. 17–17B.

In FIG. 17, an anode stack is shown comprising anode 2125 and base assembly 2150. Assembly 2150 includes conductor disc 2155, dielectric disc 2160 and base plate 2165, which in this example is shown with temperature sensor 2400 embedded therein. The anode stack is positioned horizontally in order to correlate with the distance axis (x-axis) on the graph of FIG. 17A.

As shown in FIG. 17A, the anode stack has different temperature drops across the various components comprising the stack. Beginning at the right most end of anode 2125, for both a 50 W and 25 W example, there is shown a temperature drop which has a slope slightly steeper than the temperature drop across, for example, conductor disc 2155. Although both anode 2125 and disc 2155 are conductive, the larger cross-section for disc 2155 means that there is less of a temperature drop from one main surface to the other. Also as shown in FIG. 17A, the change in temperature across the anode stack relates to the anode power level. The change in temperature (y-axis) refers to a changing temperature offset of the anode stack above room temperature. Thus, at zero applied anode power level the offset is assumed to be zero.

As a further enhancement, an x-ray source assembly in accordance with an aspect of the present invention could be adjusted to accommodate for changes in room or ambient temperature. In order for the total thermal expansion of the elements contributing to the expansion to be the same at 50 W beam current as at 0 W beam current, then the 0 W base temperature of plate 2165 (and hence the connected elements) can be raised to, for example, 40° C. This is shown in FIG. 17A by the dotted line.

FIG. 17B depicts an example of reference temperature less ambient temperature of a component of the anode stack for various anode power levels between 0 and 50 Watts. More particularly, FIG. 17B depicts the reference temperature (derived and shown at 0 W in FIG. 17A) for various tube operating powers. Further, by adding an additional temperature offset to this reference temperature, the same system can accommodate changes in ambient temperature. For example, at 50 W and 20° C., a 0° C. reference delta temperature is obtained. If this reference delta temperature is raised to 5° C., then additional heating is to be supplied to maintain this delta temperature at 20° C. However at 25° C., no additional heating is required. In this way, an offset in the reference delta temperature is required at, for example, 20° C., which allows for compensation at higher ambient temperatures.

FIG. 18 illustrates in cross-section an elevational view of one embodiment of an x-ray source assembly, generally denoted 2700, in accordance with a further aspect of the present invention. X-ray source assembly 2700 includes an x-ray source 2705 and an output optic 2135. Optic 2135 is aligned to x-ray transmission window 2107 of vacuum x-ray tube 2105. X-ray tube 2105 again houses electron gun 2115 arranged opposite to high voltage anode 2125. When voltage is applied, electron gun 2115 emits electrons in the form of an electron stream (i.e., electron beam 2120 as described above). HV anode 2125 acts as a target with respect to a source spot upon which the electron stream impinges for producing x-ray radiation 2130 for transmission through window 2107 and collection by optic 2135. Electron gun 2115 and anode 2125 function as described above in connection with the embodiments of FIGS. 12, 14 & 15.

Anode 2125 is again physically and electrically connected to a base assembly which includes a conductor plate 2155 that is electrically isolated from a base plate 2165' via a dielectric disc 2160. The construction and function of the base assembly could be similar to the base assemblies described above in connection with FIGS. 12, 14 & 15. A high voltage lead 2170 connects to conductive plate 2155 to provide the desired power level to anode 2125. The electron gun 2115, anode 2125, base assembly 2150 and high voltage lead 2170 are encased by encapsulant 2175 all of which reside within a housing 2710. Housing 2710 includes an aperture 2712 aligned to x-ray transmission window 2107 of x-ray tube 2105. In operation, x-ray radiation 2130 is collected by optic 2135, and in this example, focused 2740 to a spot 2745. As noted above, optic 2135 may comprise any one of various types of optical elements, including polycapillary bundles and doubly curved crystals. Also, optic 2135 may, for example, comprise a focusing optic or a collimating optic depending upon the application for the x-ray source assembly.

In accordance with an aspect of the present invention, a control system is implemented within x-ray source assembly 2700. This control system includes, for example, a processor 2715, which is shown embedded within housing 2710, as well as one or more sensors and one or more actuators (such as sensor/actuator 2720 and actuator 2730), which would be coupled to processor 2715. This control system within x-ray source assembly 2700 comprises functionality to compensate for, for example, thermal expansion of HV anode 2125 and base assembly 2150 with changes in anode power level in order to maintain an alignment of x-rays 2130 with respect to optic 2135. This enables the x-ray source assembly 2700 to maintain a spot size 2745 with stable intensity within a range of anode operating levels.

Figure 19:
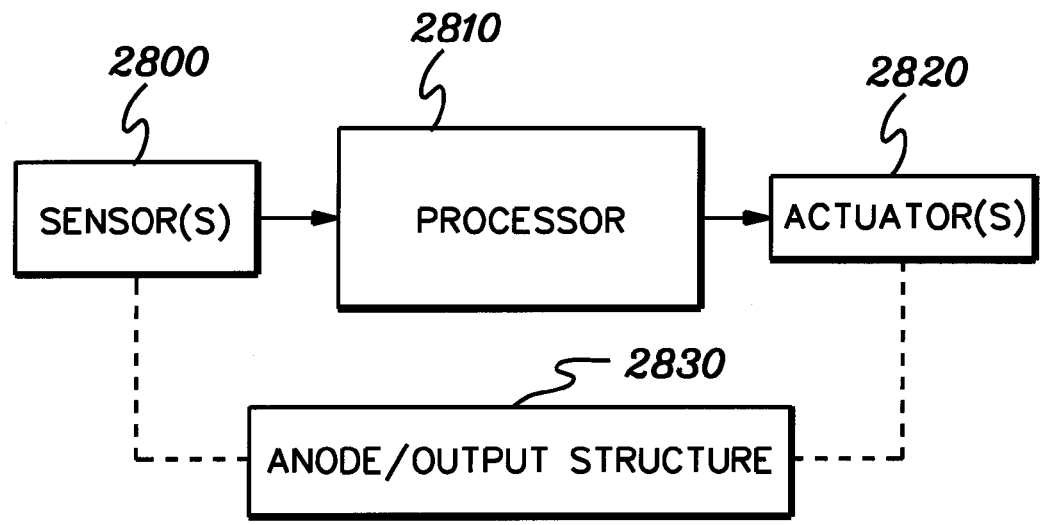
FIG. 19 depicts a block diagram of one embodiment of a control system for an x-ray source assembly, in accordance with an aspect of the present invention.
Figure 19A:
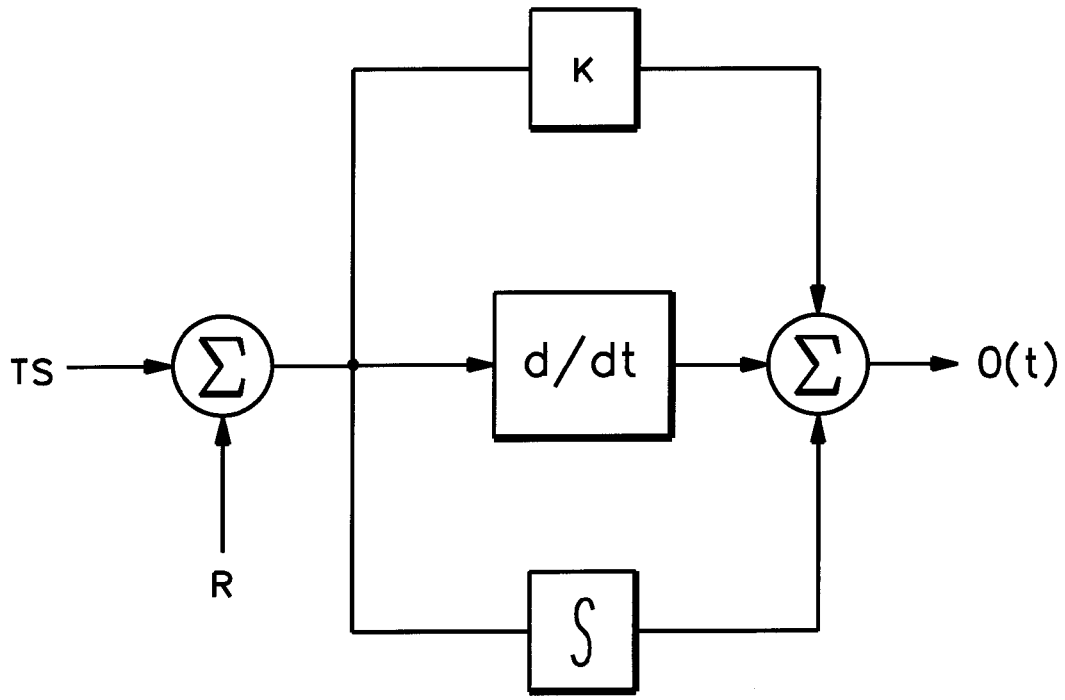
FIG. 19A is a representation of one embodiment of processing implemented by the processor of the control system of FIG. 19, in accordance with an aspect of the present invention.

FIG. 19 depicts one embodiment of a control loop and FIG. 19A depicts one example of a control function, in accordance with an aspect of the present invention. As shown in FIG. 19, one or more sensors 2800 provide feedback on, for example, anode stack temperature and/or x-ray output intensity, which is fed to a processor 2810 implementing the control function. By way of example, FIG. 19A depicts a control function wherein a temperature offset is determined between the value from a temperature sensor (TS) and a reference temperature (R) in order that the current position (K), rate of change (d/dt) and accumulated history (S) can be determined. The results of this proportional integral derivative function are then summed to provide an output as a function of time (O(t)). This output is provided to one or more actuators 2820 which effect an automatic change in either the anode source spot location or the location of an output structure (such as the optic), in order that for example, the anode source spot location is maintained relative to the output structure or output intensity of the optic is held to a desired value. This monitoring and adjustment process could be continuously repeated by the control system of the x-ray source assembly.

Returning to FIG. 18, sensor/actuator 2720 could include a temperature actuator physically coupled to base plate 2165'. This temperature actuator 2720 could comprise for example, any means for applying heat and/or applying cooling to base plate 2165' in order to add/remove heat to/from the base plate. By way of example, the heating element might comprise a 10 Ohm power resistor such as model number MP850 available from Caddock Electronics of Riverside, Calif., while an appropriate cooling element might comprise a forced air heat sink or a liquid based heat sink. The temperature actuator can be utilized during operation of the x-ray source assembly to maintain the anode x-ray spot at an optimum orientation with respect to one or more output structures such as the x-ray collection optic. The application of heat or removal of heat from the base plate is accomplished so that a consistent average temperature is maintained across the anode stack throughout operation of the x-ray source assembly notwithstanding change in one or more operating conditions of the assembly, such as anode power level.

Specifically, in one embodiment, the thermal expansion of the base assembly and HV anode are maintained within a tolerance that enables the generated x-rays to be consistently aligned with, for example, the collection optic throughout the operating ranges of the x-ray source assembly. The addition of applied heat may occur, for example, when the x-ray source assembly shifts to a reduced operating power so that the HV anode and the base assembly elements do not undergo a reduction in size due to a reduced dissipation of heat therethrough, enabling an optimum alignment of x-rays and the collection optic to be maintained. In one embodiment, the heating element could be included internal to the base plate, while the cooling element might be thermally coupled to the exposed surface of the base plate.

Although described herein in connection with maintaining a consistent average temperature across the anode stack, those skilled in the art will recognize that there are other mechanisms for maintaining the desired alignment between the anode source spot and the output structure. For example, mechanical actuator(s) 2730 could be employed to physically adjust the orientation and positioning of the collection optic relative to the anode source spot. These actuators could be manually adjustable or automated so as to be responsive to a signal received from processor 2715. Other actuation control mechanisms will also be apparent to those skilled in the art and are encompassed by the claims presented herein. The goal of the control system is to maintain a desired orientation of the anode source spot relative to, e.g., the collection optic input (i.e., focal point). Typically, this desired orientation will comprise the optimum orientation which ensures the highest intensity spot 2745.

Figure 20:
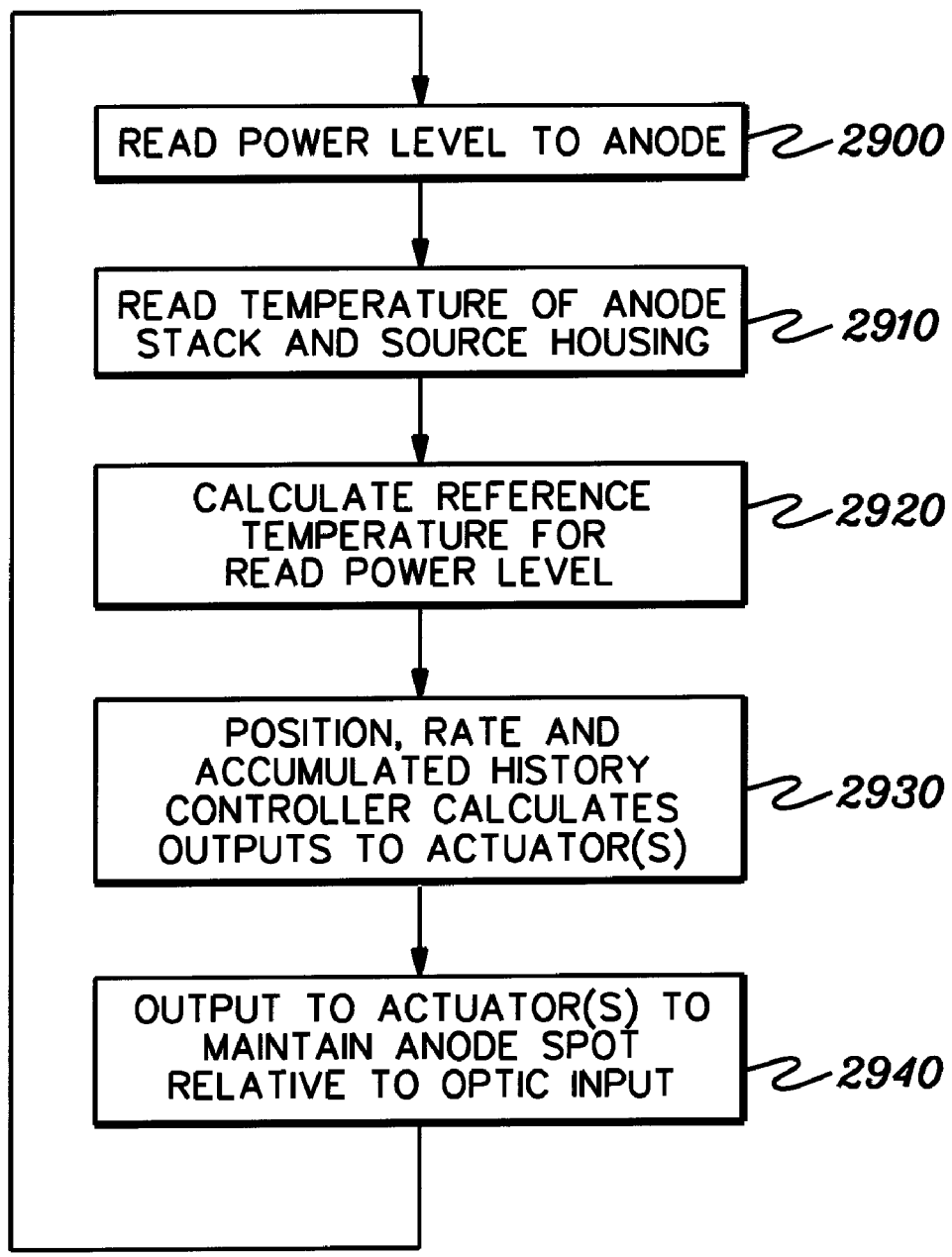
FIG. 20 is a flowchart of one embodiment of control processing for an x-ray source assembly, in accordance with an aspect of the present invention.

FIG. 20 is a flowchart of one embodiment of processing which may be implemented by processor 2715 of FIG. 18. FIG. 20 represents a loop which is periodically repeated by the processor during operation of the x-ray source assembly to, for example, apply or remove heat from the base assembly in response to a change in one or more operating conditions, such as the power level applied to the anode, and thereby maintain a consistent average temperature across the anode stack and thus enable the emitted x-rays to be optimally aligned with respect to the input of the collection optic.

As shown in FIG. 20, processing begins by reading the anode power level 2900. In one embodiment, the anode power level can be determined from two analog inputs whose signals range, for example, between 0 and 10 V. One input communicates the voltage at which the power supply supplying power to e-gun 2115 (FIG. 18) is operating, while a second input communicates the amperage being drawn by the power supply. From these two inputs, the power at which e-gun 2115 is operating may be determined, which is also the power level of the anode.

Processing next reads the temperature of the anode stack as well as the source housing 2910. As noted above, the temperature of the anode stack can be obtained from the base plate of the base assembly using a temperature sensor, with the resultant signal fed back to the processor embedded within the assembly. The housing temperature also could comprise a temperature sensor, which in one embodiment, would be thermally coupled to a surface of the housing in order to measure expansion or contraction of the enclosure. The desirability of measuring housing temperature assumes that the optic or other output structure being monitored is mechanically coupled to the housing.

Next, processing determines a reference temperature for the read power level 2920. The reference temperature would be a desirable predetermined temperature for the anode stack at the measured anode power level. Reference temperatures could be determined during a calibration procedure for the x-ray source assembly, and may either be unique to a particular assembly or generic to a plurality of identically manufactured x-ray source assemblies. FIG. 21 depicts one embodiment of a table which could be employed in order to look up the reference temperature for a read power level. As shown, the table of FIG. 21 also employs the housing temperature as another operating condition to be considered in determining the desired reference temperature for the anode stack. Thus, depending upon the housing temperature for the x-ray source assembly and the anode power level, a desired reference temperature for the anode stack is obtained.

The reference temperature and the read temperatures are fed to a position, rate and accumulated history control algorithm such as described above in connection with FIG. 19. The algorithm is employed to calculate the outputs to the one or more actuators 2930. One of ordinary skill in the art can readily implement a proportion integral derivative algorithm to accomplish this function. Once the output is obtained, the output is provided to the actuator(s) in order to, for example, maintain the anode source spot location relative to the optic input 2940.

As one specific example, the processor could output a signal which comprises a pulse width modulated signal that enables the cooling fan to operate at a range of rotational speeds, and thereby remove heat at an appropriate rate from the base plate of the anode stack. The duty cycle is such a pulse width modulated output can be determined by the operating power of the anode. A second output could enable variation in the power supplied to the heating element, and thereby variations in the amount of heat added to the base plate of the anode stack. In one embodiment, the processor, after performing the proportional integral differential (PID) algorithm, could utilize a formula or a look-up table to determine the temperature that the base plate of the anode stack should be maintained at (i.e., reference temperature) for a particular power level at which the anode is currently operating.

As an alternative to the above-described feedback based algorithm, the processor could implement (by way of example) a model or predictive based algorithm. As an example of a predictive based algorithm, the source and optic could be intentionally misaligned in order to identify an accurate starting position on a known source scan curve. For example, the source and optic alignment could be misplaced to a high slope position on the source scan curve, thereby allowing the displacement to be accurately measured or inferred. Thereafter, using the determined displacement, an adjustment can be made using the known source scan curve to return to the peak of the curve.

While the invention has been particularly shown and described with reference to preferred embodiment, it will be understood by those skilled in the art that various changes in form and details may be made to the invention without departing from the spirit and scope of the invention described in the following claims.

The invention claimed is:

1. An x-ray source assembly for directing x-rays toward a sample comprising:
an x-ray tube including an anode having a source spot upon which electrons impinge;
an x-ray output structure of the x-ray source assembly; and
a control system for controllably positioning the anode source spot relative to the output structure of the x-ray source assembly, wherein the control system maintains the anode source spot location relative to the output structure notwithstanding a change in at least one operating condition of the x-ray source assembly.

2. The x-ray source assembly of claim 1, wherein the control system includes at least one actuator for effecting movement of at least one of the anode source spot and the output structure.

3. The x-ray source assembly of claim 1, wherein the control system further includes at least one sensor for providing feedback related to the anode source spot location relative to the output structure.

4. The x-ray source assembly of claim 1, wherein the output structure comprises an optic for collecting x-rays generated by the anode.

5. The x-ray source assembly of claim 4, wherein the optic comprises at least one of a focusing optic and a collimating optic.

6. The x-ray source assembly of claim 4, wherein the optic comprises one of a polycapillary optic or a doubly curved crystal.

7. The x-ray source assembly of claim 1, wherein the at least one operating condition, over which the control system maintains the anode source spot location, comprises anode power level.

8. The x-ray source assembly of claim 1, wherein the at least one operating condition, over which the control system maintains the anode source spot location, comprises ambient temperature about the x-ray source assembly.

9. The x-ray source assembly of claim 1, wherein the at least one operating condition, over which the control system maintains the anode source spot location, comprises a housing temperature of the x-ray source assembly.

10. The x-ray source assembly of claim 1, wherein the control system maintains the displacement of the anode source spot to optic such that output intensity is within 99% of maximum output intensity for a supplied anode power level.

11. The x-ray source assembly of claim 1, wherein the control system dynamically controls position of the anode source spot relative to the output structure during operation of the x-ray source assembly.

12. The x-ray source assembly of claim 1, further comprising:
a thermally-conductive, dielectric material thermally coupled to the anode for removing heat generated by the anode.

13. An x-ray source assembly comprising:
an x-ray tube including an anode having a source spot upon which electrons impinge;
an output structure of the x-ray source assembly; and
a control system for controlling position of the anode source spot relative to the output structure, wherein the control system maintains the anode source spot location relative to the output structure notwithstanding a change in at least one operating condition of the x-ray source assembly,
wherein the control system includes at least one actuator for effecting movement of at least one of the anode source spot and the output structure, and wherein the at least one actuator comprises a temperature actuator for performing at least one of heating and cooling of the anode and thereby effectuating adjustment of the anode source spot location relative to the output structure.

14. An x-ray source assembly comprising:
an x-ray tube including an anode having a source spot upon which electrons impinge;
an output structure of the x-ray source assembly; and
a control system for controlling position of the anode source spot relative to the output structure, wherein the control system maintains the anode source spot location relative to the output structure notwithstanding a change in at least one operating condition of the x-ray source assembly,
wherein the control system includes at least one actuator for effecting movement of at least one of the anode source spot and the output structure, and wherein the at least one actuator comprises at least one mechanical actuator for adjusting position of at least one of the anode source spot and the output structure.

15. An x-ray source assembly comprising:
an x-ray tube including an anode having a source spot upon which electrons impinge;
an output structure of the x-ray source assembly; and
a control system for controlling position of the anode source spot relative to the output structure, wherein the control system maintains the anode source spot location relative to the output structure notwithstanding a change in at least one operating condition of the x-ray source assembly, wherein the control system further includes at least one sensor for providing feedback related to the anode source spot location relative to the output structure, and wherein the at least one sensor comprises a sensor for monitoring anode power level.

16. An x-ray source assembly comprising:
an x-ray tube including an anode having a source spot upon which electrons impinge;
an output structure of the x-ray source assembly; and
a control system for controlling position of the anode source spot relative to the output structure, wherein the control system maintains the anode source spot location relative to the output structure notwithstanding a change in at least one operating condition of the x-ray source assembly,
wherein the control system further includes at least one sensor for providing feedback related to the anode source spot location relative to the output structure, and wherein the at least one sensor comprises at least one sensor for directly or indirectly monitoring anode temperature.

17. An x-ray source assembly comprising:
an x-ray tube including an anode having a source spot upon which electrons impinge;
an output structure of the x-ray source assembly; and
a control system for controlling position of the anode source spot relative to the output structure, wherein the control system maintains the anode source spot location relative to the output structure notwithstanding a change in at least one operating condition of the x-ray source assembly,
wherein the control system further includes at least one sensor for providing feedback related to the anode source spot location relative to the output structure, and
the x-ray source assembly further comprising a housing at least partially enclosing the anode, and wherein the at least one sensor comprises at least one sensor for measuring temperature of the housing.

18. An x-ray source assembly comprising:
an x-ray tube including an anode having a source spot upon which electrons impinge;
an output structure of the x-ray source assembly; and
a control system for controlling position of the anode source spot relative to the output structure, wherein the control system maintains the anode source spot location relative to the output structure notwithstanding a change in at least one operating condition of the x-ray source assembly,
wherein the control system further includes means for:
obtaining anode power level;
obtaining at least one of anode temperature, temperature of a housing surrounding the anode, and ambient temperature about the x-ray source assembly;
determining a reference temperature for the obtained anode power level; and
controlling anode source spot location relative to the output structure employing the reference temperature and at least one of the anode temperature and the housing temperature.

19. The x-ray source assembly of claim 18, wherein the means for controlling comprises means for automatically controlling anode source spot location relative to the output structure notwithstanding variation in the at least one operating condition of the x-ray source assembly.

20. An apparatus for analyzing a fluid using x-rays, the apparatus comprising:
means for exposing the fluid to x-rays to cause at least one component of the fluid to x-ray fluoresce;
means for analyzing the x-ray fluorescence from the fluid to determine at least one characteristic of the fluid; and
an x-ray source assembly comprising:
an x-ray tube including an anode having a source spot upon which
electrons impinge;
an output structure of the x-ray source assembly; and
a control system for controlling position of the anode source spot relative to the output structure, wherein the control system maintains the anode source spot location relative to the output structure notwithstanding a change in at least one operating condition of the x-ray source assembly.

21. The combination of claim 20, wherein the at least one characteristic of the fluid comprises a concentration of at least one component in the fluid.

22. The combination of claim 20, wherein the fluid comprises a fluid stream.

23. The combination of claim 20, wherein the means for exposing and/or the means for analyzing comprises at least one x-ray focusing or collimating optic for focusing x-rays to or from the fluid.

24. An x-ray source assembly comprising:
an x-ray tube including an anode having a source spot upon which electrons impinge;
an output structure of the x-ray source assembly; and
a control system for controlling position of the anode source spot relative to the output structure, wherein the control system maintains the anode source spot location relative to the output structure notwithstanding a change in at least one operating condition of the x-ray source assembly,
the x-ray source assembly further comprising:
a housing at least partially enclosing an x-ray tube including the anode;
an adjustable mounting means for mounting the x-ray tube to the housing;
wherein the adjustable mounting means allows locational adjustment of the x-ray tube in the housing to optimize transmission of x-rays therefrom.

25. The x-ray source assembly of claim 24, wherein the adjustable mounting means comprises a plurality of threaded fasteners.

26. The x-ray source assembly of claim 24, further comprising:
a housing at least partially enclosing an x-ray tube including the anode;
datum points on the housing for aligning an x-ray tube to the housing.

27. A method for providing x-rays comprising:
providing an x-ray source assembly for directing x-rays toward a sample, the assembly having an x-ray tube including an anode with a source spot upon which electrons impinge, the x-ray source assembly also including an x-ray output structure; and
controllably positioning the anode source spot relative to the output structure of the x-ray source assembly, wherein the controlling includes maintaining the anode source spot location relative to the output structure notwithstanding a change in at least one operating condition of the x-ray source assembly.

28. The method of claim 27, wherein the controlling comprises automatically controlling position of at least one of the anode source spot and the output structure in order to maintain the anode source spot location relative to the output structure notwithstanding change in at least one operating condition of the x-ray source assembly.

29. The method of claim 28, wherein the controlling comprises sensing at least one variable related to the anode source spot location relative to the output structure.

30. The method of claim 29, wherein the at least one variable comprises at least one of anode power level, anode temperature, temperature of a housing at least partially surrounding the anode, or ambient temperature about the x-ray source assembly.

31. The method of claim 27, wherein the output structure comprises an optic for collecting x-rays generated by the anode.

32. The method of claim 31, wherein the optic comprises at least one of a focusing optic and a collimating optic.

33. The method of claim 27, wherein the at least one operating condition, over which the anode source spot location is maintained, comprises anode power level; ambient temperature about the x-ray source assembly; or a housing temperature of the x-ray source assembly.

34. The method of claim 27, further comprising:
using a thermally-conductive, dielectric material thermally coupled to anode for removing heat generated by the x-ray tube.

35. A method of analyzing a fluid using x-rays, method comprising:
exposing the fluid to x-rays to cause at least one component of the fluid to x-ray fluoresce;
analyzing the x-ray fluorescence from the fluid to determine at least one characteristic of the fluid; and
providing the x-rays, comprising:
providing an x-ray source assembly having an x-ray tube including an anode with a source spot upon which electrons impinge, the x-ray source assembly also including an output structure; and
controlling position of the anode source spot relative to the output structure, wherein the controlling includes maintaining the anode source spot location relative to the output structure notwithstanding a change in at least one operating condition of the x-ray source assembly.

36. An x-ray source assembly comprising:
an x-ray tube having an anode for generating x-rays;
an optic for collecting x-rays generated by the anode;
the assembly enclosing the x-ray tube and the optic from which x-rays are emitted by the optic; and
a control system for controlling x-ray output intensity of the optic, wherein the control system can maintain said x-ray output intensity notwithstanding a change in at least one operating condition of the x-ray source assembly.

37. The x-ray source assembly of claim 36, wherein the control system further includes a sensor for monitoring x-ray output intensity of the optic and a controller for controlling position of at least one of the anode and the optic using monitored x-ray output intensity.

38. The x-ray source assembly of claim 37, wherein the controller comprises at least one actuator, the at least one actuator comprising at least one temperature actuator or mechanical actuator for effectuating adjustment of the anode location relative to the optic and therein control of x-ray output intensity from the optic.

39. The x-ray source assembly of claim 36, wherein the optic comprises one of a focusing optic and a collimating optic.

40. The x-ray source assembly of claim 36, wherein the optic comprises one of a polycapillary optic or a doubly curved crystal.

41. The x-ray source assembly of claim 36, wherein the optic comprises one of a pinhole, a slit or a filter.

42. The x-ray source assembly of claim 36, wherein the at least one operating condition comprises anode power level.

43. The x-ray source assembly of claim 36, wherein the at least one operating condition comprises an ambient temperature about the x-ray source assembly.

44. The x-ray source assembly of claim 36, wherein the at least one operating condition comprises a housing temperature of the x-ray source assembly.

45. The x-ray source assembly of claim 36, wherein control system comprises an automatic control system for controlling x-ray output intensity of the optic, and wherein the control system is feedback or predictive based.

46. The x-ray source assembly of claim 45, wherein the control system automatically maintains the x-ray output intensity of the optic within 1% of a peak intensity value for a supplied anode power level.

47. The x-ray source assembly of claim 36, wherein the control system maintains x-ray output intensity by controlling at least one of temperature of the anode and position of the anode relative to the optic.

48. The x-ray tube assembly of claim 36 in combination with an apparatus for analyzing a fluid using x-rays, the apparatus comprising:
means for exposing the fluid to x-rays to cause at least one component of the fluid to x-ray fluoresce; and
means for analyzing the x-ray fluorescence from the fluid to determine at least one characteristic of the fluid.

49. The combination of claim 48, wherein the at least one characteristic of the fluid comprises a concentration of at least one component in the fluid.

50. The combination of claim 48, wherein the fluid comprises a fluid stream.

51. The combination of claim 48, wherein the means for exposing and/or the means for analyzing comprises at least one x-ray focusing or collimating optic for focusing x-rays to or from the fluid.

52. The x-ray source assembly of claim 36, further comprising:
a thermally-conductive, dielectric material thermally coupled to the x-ray tube for removing heat generated by the x-ray tube.

53. The x-ray source assembly of claim 36, wherein the control system further includes means for:
obtaining anode power level;
obtaining at least one of anode temperature, temperature of a housing surrounding the anode, and ambient temperature about the x-ray source assembly;
determining a reference temperature for the obtained anode power level; and
controlling anode source spot location relative to the output structure employing the reference temperature and at least one of the anode temperature and the housing temperature.

54. The x-ray source assembly of claim 53, wherein the means for controlling comprises means for automatically controlling anode source spot location relative to the output structure notwithstanding variation in the at least one operating condition of the x-ray source assembly.

55. The x-ray source assembly of claim 36, wherein the control system maintains the displacement of the anode source spot to optic such that output intensity is within 99% of maximum output intensity for a supplied anode power level.

56. The x-ray source assembly of claim 36, wherein the control system dynamically controls position of the anode source spot relative to the output structure during operation of the x-ray source assembly.

57. The x-ray source assembly of claim 36, further comprising
   a housing at least partially enclosing the x-ray tube;
   an adjustable mounting means for mounting the x-ray tube to the housing;
   wherein the adjustable mounting means allows locational adjustment of the x-ray tube in the housing to optimize transmission of x-rays therefrom.

58. The x-ray source assembly of claim 57, wherein the adjustable mounting means comprises a plurality of threaded fasteners.

59. The x-ray source assembly of claim 57, further comprising: a housing at least partially enclosing the x-ray tube; datum points on the housing for aligning the x-ray tube to the housing.

* * * * *